United States Patent [19]
Terase et al.

[11] Patent Number: 6,077,341
[45] Date of Patent: Jun. 20, 2000

[54] SILICA-METAL OXIDE PARTICULATE COMPOSITE AND METHOD FOR PRODUCING SILICA AGGLOMERATES TO BE USED FOR THE COMPOSITE

[75] Inventors: Kunihiko Terase; Masaharu Tanaka; Masaki Inoue; Eiichi Ono; Takayoshi Sasaki, all of Kitakyushu, Japan

[73] Assignees: Asahi Glass Company, Ltd., Tokyo; Dohkai Chemical Industry Co., Ltd., Kitakyushu, both of Japan

[21] Appl. No.: 09/161,386

[22] Filed: Sep. 28, 1998

[30] Foreign Application Priority Data

Sep. 30, 1997 [JP] Japan .................................. 9-281090
Dec. 22, 1997 [JP] Japan .................................. 9-364855

[51] Int. Cl.[7] .............................. C09C 1/04; C09C 1/24; C09C 1/28; C09C 1/36
[52] U.S. Cl. ...................... 106/482; 106/425; 106/436; 106/444; 106/446; 106/454; 106/482; 106/492
[58] Field of Search ................................. 106/425, 436, 106/444, 446, 454, 482, 492; 502/239, 243

[56] References Cited

U.S. PATENT DOCUMENTS 4,090,887  5/1978  Marquisee et al. ................. 106/288 B
5,298,065  3/1994  Hiraoka et al. ......................... 106/425

OTHER PUBLICATIONS

Patent Abstracts of Japan, vol. 097, No. 009, Sep. 30, 1997, JP 09 132514, May 20, 1997.

Patent Abstracts of Japan, vol. 097, No. 007, Jul. 31, 1997, JP 09 071417, Mar. 18, 1997.

Patent Abstracts of Japan, vol. 097, No. 006, Jun. 30, 1997, JP 09 030933, Feb. 4, 1997.

Patent Abstracts of Japan, vol. 095, No. 011, Dec. 26, 1995, JP 07 228515, Aug. 29, 1995.

Patent Abstracts of Japan, vol. 016, No. 419 (C–0981), Sep. 3, 1992, JP 04 145011, May 19, 1992.

*Primary Examiner*—Karl Group
*Assistant Examiner*—Michael J. DiVerdi
*Attorney, Agent, or Firm*—Oblon, Spivak, McClelland, Maier & Neustadt, P.C.

[57] ABSTRACT

A silica-metal oxide particulate composite comprising silica agglomerates having voids formed by random stacking of scaly silica primary particles, and metal oxide particulates supported on the surfaces, and the inner surfaces in the voids, of the silica agglomerates.

20 Claims, 4 Drawing Sheets

SILICA-METAL OXIDE PARTICULATE COMPOSITE AND METHOD FOR PRODUCING SILICA AGGLOMERATES TO BE USED FOR THE COMPOSITE

The present invention relates to a silica-metal oxide particulate composite, wherein metal oxide particulates having an ultraviolet ray-shielding function, etc., are supported on the surface of silica agglomerates composed of scaly silica. Further, the present invention relates to a method for producing silica agglomerates composed of scaly silica, which are useful for forming such a silica-metal oxide particulate composite.

In recent years, attention has been drawn to hazards of ultraviolet rays to the skin along with the problem of destruction of the ozone layer. As a result of recent dermatological researches, it has been found that ultraviolet rays present adverse effects more than expected in various aspects such that if the skin is exposed to ultraviolet rays repeatedly for a long period of time, collagen fibers of the skin tissue tend to be destroyed, which causes formation of fine wrinkles, chromatosis such as stains or freckles and aging of the skin, and in the worst case, the gene of skin cells may be injured, which leads to a danger of inducing carcinoma cutaneum.

Further, not only the organism, but also resins and coating materials undergo deterioration with time by direct oxidation action of ultraviolet rays, if they are exposed to the direct rays of the sun so that they are subject to influence of ultraviolet rays.

Particulates of a metal oxide such as titanium dioxide, zinc oxide, cerium oxide or iron oxide, are known to be a substance having a substantial effect for shielding ultraviolet rays. However, as they are fine particles, they tend to readily agglomerate, and it is practically difficult to uniformly or homogeneously disperse them in a cosmetic, a coating material or a resin. Further, especially when incorporated to a cosmetic material, they have brought about problems such that the spreadability tends to be poor, and the feeling on application tends to be poor. Further, some of them have photocatalytic oxidation activities, and if incorporated as they are to e.g. a cosmetic, a coating material or a resin, they have brought about a problem that they tend to oxidize the constituting components such as oil and fat, a perfume, a dye, a resin, etc., thus leading to deterioration, modification or discoloration.

Heretofore, to solve such problems, there have been some proposals for a technique of incorporating such particulates of a metal oxide such as titanium dioxide into silica (e.g. Japanese Patent No. 2591946 and JP-B-5-75684). However, in reality, it is not easy to uniformly incorporate particulates into silica with good reproducibility or to control the dispersed state of silica and titanium dioxide, and the initial purpose has not necessarily been accomplished.

Further, more essentially, there is a problem that silica particles disclosed here are amorphous and extremely brittle from the viewpoint of the strength.

It is already known (for example, in JP-A-2-258615) that scaly silica can be produced by a method different from the above-mentioned method, and the present inventors have previously proposed (i.e. in Japanese Patent Application No. 9-179121) a technique which is more suitable for industrial production to incorporate and combine particulates of a metal oxide such as titanium dioxide by means of scaly silica.

The object of the present invention is to provide a composite having the above problems solved by using agglomerates composed of scaly silica, as a matrix, and by supporting on the surfaces, and on the inner surfaces in voids, of the matrix, metal oxide particulates which are extremely susceptible to agglomeration and of which the catalytic reaction activities can hardly be controlled.

Under these circumstances, the present inventors have conducted an extensive study and as a result, have found that a mere mixture obtained by mechanically mixing scaly silica with particulates of a metal oxide such as titanium dioxide or zinc oxide, has an excellent ultraviolet ray-shielding function, and to their surprise, they have found an unexpected phenomenon such that despite such titanium oxide or the like is not substantially included in the scaly silica, decomposition or deterioration of an organic compound due to a photocatalytic oxidation action which is naturally expected, is very little.

From a further study in detail, they have also found another unexpected phenomenon such that this scaly silica has agglomerated to form agglomerates of a specific shape having numerous voids, and the metal oxide particulates are present in such a state that they are supported on the surfaces, and the inner surfaces in the voids, of such silica agglomerates. The present invention has been accomplished on the basis of such discoveries.

That is, the present invention provides a silica-metal oxide particulate composite comprising silica agglomerates having voids formed by random stacking of scaly silica primary particles, and metal oxide particulates supported on the surfaces, and the inner surfaces in the voids, of the silica agglomerates.

Figure 1:
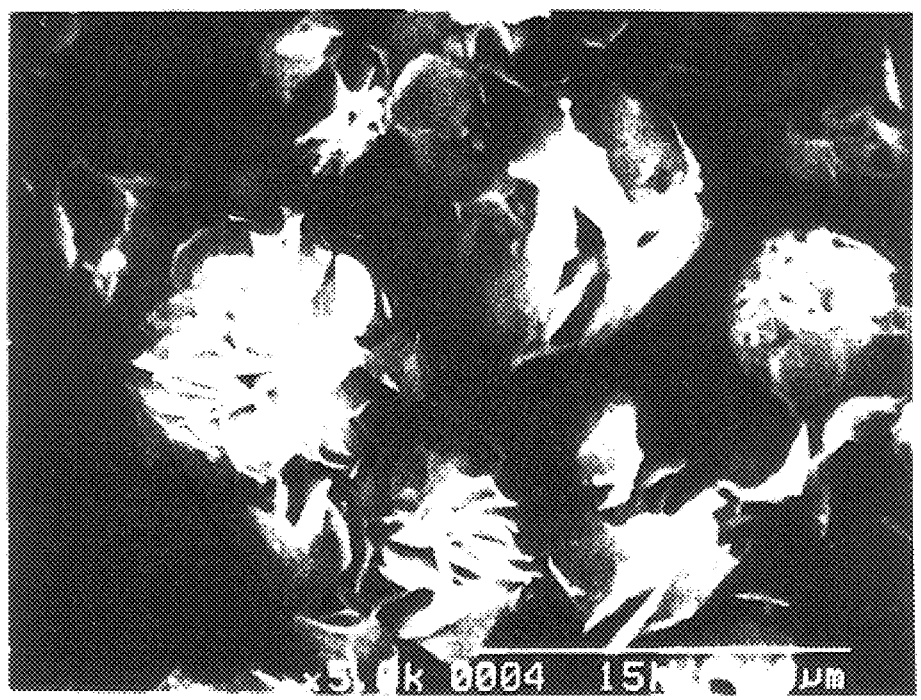
FIG. 1 is a scanning electron microscopic photograph showing the particle structures of silica agglomerates.

Now, the present invention will be described in detail with reference to the preferred embodiments.

Firstly, the metal oxide particulates will be described.

The metal oxide particulates are preferably particulates of a metal oxide other than silica, and they may, for example, be preferably titanium dioxide, titanium peroxide, zinc oxide, cerium oxide, ferrous oxide, ferric oxide, zirconium oxide, chromium oxide, aluminum oxide, magnesium oxide, silver oxide, cuprous oxide, cupric oxide, cobaltous oxide, tricobalt tetroxide, cobaltic oxide, nickelous oxide, nickelic oxide, thorium oxide, tungsten oxide, molybdenum oxide, manganese dioxide, manganese trioxide, uranium oxide, thorium oxide, germanium oxide, stannous oxide, stannic oxide, lead monoxide, trilead tetroxide, lead dioxide, antimony trioxide, antimony pentoxide or bismuth trioxide. They may be selected for use depending upon the particular purpose. For example, in a case where a substantial ultraviolet ray-shielding function is required, particulates of titanium dioxide, zinc oxide, cerium oxide or iron oxide, are preferred. Further, in a case where an infrared ray-shielding function is required, particulates of tin oxide are preferred. They may be used alone or in combination as a mixture of two or more of them.

The particulates of a metal oxide in the present invention, include those which are so-called ultrafine particles, and they have a primary particle size (particle diameter) of from 0.002 to 0.5 µm, preferably from 0.01 to 0.5 µm, more preferably from 0.03 to 0.3 µm. If the primary particle size is less than 0.002 µm, the specific surface area increases, and particulates will be in an agglomerated state from the beginning, and it tends to be difficult to add and mix the particulates to the silica agglomerates in a sufficiently dispersed state, whereby the desired ultraviolet ray-shielding function tends to be hardly obtainable. On the other hand, if it exceeds 0.5 µm, not only the ultraviolet ray-shielding function of the particulates themselves lowers, but also it tends to be difficult to have the particulates of the metal oxide supported stably on the surfaces, or the inner surfaces in the voids, of the silica agglomerates as the matrix.

The particle form of the particulates of a metal oxide in the present invention is basically preferably spherical, and in such a case, the particle size represents the diameter. However, the particulates may be non-spherical particles such as randomly shaped or needle-shaped particles, and in such a case, the particle size represents the largest diameter.

The amount of the metal oxide particulates in the composite is preferably from 1 to 80 wt %, more preferably from 1 to 50 wt %, most preferably from 2 to 35 wt % (based on the total amount of the metal oxide+silica). If the amount is less than 1 wt %, no adequate function provided by the metal oxide particulates, such as no adequate ultraviolet ray-shielding effect, can be obtained. On the other hand, if it exceeds 80 wt %, part or substantial part of the metal oxide particulates will remain not supported stably on the surfaces, or the inner surfaces in the voids, of the silica agglomerates, such being undesirable.

In a case where two components of titanium dioxide and zinc oxide are used in admixture in an application for shielding ultraviolet rays, the blend ratio is preferably within the following range from a viewpoint such that the light transmittance is desired to be high in a visible light region and low in an ultraviolet light region. Namely, the content of titanium dioxide, based on the total amount of titanium dioxide and zinc oxide, is preferably from 10 to 60 wt %, more preferably from 15 to 50 wt %, most preferably from 20 to 40 wt %.

In one preferred embodiment of the present invention, the metal oxide particulates as described above, have a function of shielding lights within a specific wavelength region, such as ultraviolet rays. Here, the function of shielding lights means a function such that lights in a specific wavelength region are absorbed and/or scattered by the particulates, so that those within a certain wavelength region among the irradiated lights, are substantially shielded. For example, it may be a function of shielding X-rays, a function of shielding visible light rays, a function of shielding infrared rays, or a function of shielding ultraviolet rays. There may be a case where the function of shielding ultraviolet rays is required to be high, while the function of shielding visible light rays is required to be as low as possible. Depending upon such requirements, the metal oxide particulates are selected and/or combined for use.

The metal oxide particulates to be used in the present invention, may be synthesized, respectively, by conventional methods. However, the respective particulates are usually available as commercial products having various particle sizes, and such commercial products may be used as they are, whereby the object of the present invention can adequately be accomplished.

The present invention is characterized in that silica agglomerates of a specific shape having voids formed by random stacking of scaly silica primary particles, are used as silica agglomerates having the above-described metal oxide particulates supported on their surfaces.

Scaly silica primary particles as units constituting the silica agglomerates, are scaly silica which has a thickness of from 0.001 to 1 µm, preferably from 0.01 to 0.5 µm, a ratio (an aspect ratio) of the maximum length of the scale to the thickness of at least 10, preferably at least 30, more preferably at least 50, and a ratio of the minimum length of the scale to the thickness of at least 3, preferably at least 10, more preferably at least 20.

If the thickness of the scale is less than 0.001 µm, the mechanical strength of the scale tends to be inadequate, such being undesirable. On the other hand, if the thickness of the scale exceeds 1 µm, when such particulates are incorporated to a cosmetic material, the spreadability tends to be inadequate, such being undesirable. Further, if the aspect ratio is less than 10, the spreadability tends to be likely inadequate, such being undesirable.

The upper limits of the ratio of the maximum length to the thickness and the ratio of the minimum length to the thickness are not particularly limited, but the former is practically at most 300, preferably at most 200, and the latter is practically at most 150, preferably at most 100.

For the purpose of the present invention, the thickness and the length of the scaly silica are meant for the average values with respect to the primary particles, unless otherwise specified.

Here, "scaly" may be a shape of substantially thin plate, which may be partially or entirely bent or curled. Such silica agglomerates themselves which are formed by stacking of scaly silica primary particles, have been already known as objects for academic researches, as so-called silica X (hereinafter sometimes refereed to also as $SiO_2$—X) or silica Y (similarly hereinafter sometimes referred to also as $SiO_2$—Y).

Namely, such silica-X or the like is an intermediate or metastable phase formed during the process for forming cristobalite or quartz by hydrothermal treatment of amorphous silica, and it is a feeble crystal phase which should be called quasi-crystalline of silica. Silica-X and silica-Y are different in their X-ray diffraction patterns, but the outer appearances of the particles as observed by an electron microscope are very similar to each other, and each of them can be suitably used for the purpose of the present invention.

In a conventional typical method for producing silica-X or like, silica gel (silica xerogel) or aerosil is, for example, used as the starting material, and such a starting material is subjected to hydrothermal treatment. Such a conventional method has had a problem that the reaction time is extremely long. For example, Heydemann who first discovered silica-X, used precipitated silica and aerosil (ultrafine particles of amorphous silica obtained by high temperature thermal decomposition of $SiCl_4$) as the starting material, whereby it took an extremely long time of from 1.5 to 24 days at 180° C. to convert the starting material to silica-X in an autoclave (Heydemann, A., Beitr. Mineral. Petrogr., 10,242–259 (1964)).

On the other hand, with respect to silica-Y, Mitsyuk et al. obtained silica-Y by using a silica gel having a specific surface area of from 600 to 700 m²/g as the starting material and subjecting it to hydrothermal treatment in a solution of e.g. NaOH at a temperature of from 145 to 155° C. for a long time (from 200 to 220 hours) (Mitsyuk, B. A. et al. Geochem. Int. 13,101–111 (1976)), and Kitahara et al. obtained silica-Y by using a silica gel (Silica gel G, manufactured by Wako Junyaku K.K.) having a specific surface area of about 600 m²/g as the starting material and subjecting it to hydrothermal treatment in a KOH solution containing NaCl at a temperature of from 150 to 160° C. also for a long time (from 70 to 170 hours) (Kitahara S. et al. Proc. Inst. Symp. Hydrotherm. React., 1st (1983)).

Thus, the method of using silica gel as the starting material and converting it to silica-X or the like by hydrothermal treatment, has had a problem that an extremely long reaction time (hydrothermal treatment time) is required, in its application on an industrial scale. Of course, it is possible to shorten the time by increasing the temperature for the hydrothermal treatment. However, in such a case, there will be a serious problem that the stability in the operational range is likely to be lost, and quartz or cristobalite is likely to form. Quartz or the like is considered to bring about a problem with respect to the safety to the organism in view of its crystal structure and thus is not suitable for use in cosmetics or the like. Thus, it is desired to develop a technique for producing agglomerates composed of silica-X or the like which is highly safe to the organism, at a lower temperature in a time sufficiently short to apply it on an industrial scale without formation of quartz or the like.

From such a viewpoint, the present inventors have previously proposed two methods which are more preferred than the conventional method of using silica gel (silica xerogel) as the starting material.

The first method is a method for producing silica-X or the like industrially in a shorter time under a stabilized condition by using as the starting material a silica sol containing specific amounts of a silica source and an alkali source i.e. an aqueous dispersion of colloidal silica and subjecting it to a hydrothermal treatment (Japanese Patent Application 9-179120). This method has a merit in that not only scaly silica primary particles, but silica agglomerates suitable for use in the present invention, which have voids formed by random stacking and mutual fusion of the scaly primary particles, can be obtained directly.

Namely, this is a method wherein a silica sol containing specific amounts of a silica source and an alkali source, is subjected to hydrothermal treatment, and the silica sol to be used, is preferably a silica sol obtained by subjecting an alkali metal silicate aqueous solution wherein the molar ratio of silica/alkali ($SiO_2/Me_2O$, wherein Me is an alkali metal such as Li, Na or K, the same applies hereinafter) is from 1.0 to 3.4 mol/mol, to removal of alkali by an ion exchange resin method or by an electrodialysis method. Here, as the alkali metal silicate aqueous solution, one obtained by diluting water glass with water as the case requires, is, for example, preferred.

The molar ratio of silica/alkali ($SiO_2/Me_2O$) of the silica sol is preferably within a range of from 3.5 to 20 mol/mol, more preferably within a range of from 4.5 to 18 mol/mol. Further, the silica concentration in the silica sol is preferably from 2 to 20 wt %, more preferably from 3 to 15 wt %.

The silica particle size in the silica sol is meant for an average particle size and is not particularly limited, but it is preferably at most 100 nm. Particularly preferred is one so-called active silicic acid having a particle size of at most 20 nm. The lower limit of the particle size is not particularly limited, but it is preferably at least 1.0 nm. If the particle size exceeds 100 nm too much, the stability of the silica sol tends to be poor, such being undesirable. The method for measuring the silica particle size is not particularly limited so long as the particle size of this range can be measured. For example, it can be measured by a laser beam scattering particle size measuring apparatus, or by scale measurement of the size of particle images photographs by a transmission electron microscope.

As the starting material, a silica sol as described above is used, and it is heated in a heated pressure container such as an autoclave to carry out hydrothermal treatment to form silica agglomerates composed of scaly silica.

The autoclave is not particularly limited with respect to its type, and it may be one equipped with at least a heating means and a stirring means, preferably equipped with a temperature-measuring means.

Further, prior to charging the silica sol into the autoclave for hydrothermal treatment, the silica concentration may be adjusted to a desired range by adding purified water such as distilled water or deionized water.

The hydrothermal treatment is carried out preferably within a temperature range of from 150 to 250° C., more preferably from 170 to 220° C., in order to bring the reaction speed as high as possible, and the crystallizing effect as small as possible.

Further, the time required for the hydrothermal treatment varies depending upon the temperature of the hydrothermal treatment or the addition or non-addition of seed crystals. However, it is usually from 5 to 50 hours, preferably from 5 to 40 hours, more preferably from 5 to 25 hours.

Further, in order to let the hydrothermal treatment proceed efficiently and to shorten the treating time, it is preferred to add seed crystals in an amount of from 0.001 to 1 wt %, although such an addition is not essential. As such seed crystals, silica-X or silica-Y may be used as it is or after pulverization as the case requires.

After completion of the hydrothermal treatment, the treated product is taken out of the autoclave and subjected to filtration and washing with water. The particles after treatment by washing with water are preferably such that the pH when formed into an aqueous slurry of 10 wt % is from 5 to 9, more preferably from 6 to 8.

On the other hand, the second method is a method of using a silica hydrogel as the starting material and subjecting it to hydrothermal treatment, and it is a more preferred method, since it is thereby possible to produce silica-X or the like by a reaction at a lower temperature in a shorter time without formation of crystals such as quartz and yet in good yield.

The silica hydrogel suitable for use here is a particulate silica hydrogel. The particle shape of the silica hydrogel may be spherical or a non-specific particle shape, and the method for its preparation can be optionally selected.

Taking a spherical silica hydrogel as an example, as is known since long before, it may be formed by solidifying a silica hydrosol in a spherical shape in a medium of petroleum or the like. However, more preferably, as disclosed in JP-B-48-13834, it may be produced by a method wherein an aqueous alkali metal silicate solution and an aqueous mineral acid solution are mixed to form a silica sol in a short time and at the same time, the silica sol is discharged in a gas medium and gelled in the gas.

Namely, an aqueous alkali metal silicate solution and an aqueous mineral acid solution are introduced from separate inlets into a container provided with a discharge outlet, so that they are instantaneously uniformly mixed to form a silica sol having a $SiO_2$ concentration of at least 130 g/l and a pH of from 7 to 9, which is immediately discharged from the discharge outlet into a gas medium such as air, so that it is gelled in air while it is still in air in a parabolic orbit. An aging tank containing water is placed at the falling site, and the fallen gel is aged here for from a few minutes to a few tens minutes.

An acid is added thereto to lower the pH, followed by washing with water to obtain a product, which is a spherical silica hydrogel suitable for use in the present invention.

The obtained silica hydrogel is spherical particles having a uniform particle size of from 2 to 6 mm, being transparent and having resiliency, and in a typical example, such a silica hydrogel is one containing water as much as about 4 times by weight relative to $SiO_2$ (i.e. 20 wt % of $SiO_2$ and about 80 wt % of water). The silica hydrogel particles are agglomerates of numerous silica primary particles having a particle size of about a few nm, and it is assumed that water is present on the surfaces and spaces of such primary particles. The $SiO_2$ concentration in the silica hydrogel useful in the present invention is at a level of from 15 to 75 wt % (i.e. water content: 85 to 25 wt %) from the viewpoint of the availability and the reactivity, and the water content may be adjusted within this range by drying as the case requires. Further, the water content in the hydrogel in the present invention is the one measured as follows. Namely, the silica hydrogel sample is dried at 180° C. for 2 hours, hereupon the weight of the remaining sample is taken as the amount of absolutely dry $SiO_2$, and the weight reduction is taken as the water content in the sample hydrogel.

Industrially produced and marketed dry silica gel (silica xerogel) is one obtained by sufficiently drying such silica hydrogel particles by e.g. a dryer at a temperature of from about 150 to 180° C. to remove the hydrogel water in the spaces and on the surfaces. In the above-mentioned conventional method for producing silica-X or silica-Y, this dry silica gel is used as the starting material silica for the hydrothermal treatment.

Such a silica hydrogel is used as a starting material, and it is heated in the same manner as in the first method, in a heated pressure container such as an autoclave to carry out hydrothermal treatment to form silica agglomerates in which scaly silica primary particles are randomly stacked.

In such a case, this spherical silica hydrogel may be used as it is. However, it is preferred to pulverize or roughly pulverize it to a particle size of from 0.1 to 3 mm, so that stirring in the autoclave can more efficiently be carried out.

When the silica hydrogel is charged into an autoclave for hydrothermal treatment, it is preferred to adjust the silica hydrogel concentration to a desired range by adding purified water such as distilled water or deionized water. The total silica concentration in the treatment liquid in the autoclave is selected taking the stirring efficiency, the crystal-growing speed, the yield, etc., into consideration, but it is usually from 1 to 30 wt %, preferably from 10 to 20 wt %, as $SiO_2$ based on the entire charged starting material. Here, the total silica concentration in the treating liquid means the total silica concentration in the system and includes not only silica in the silica hydrogel but also, when sodium silicate or the like is used as an alkali metal salt, silica brought into the system by such sodium silicate or the like. Further, the total silica concentration can be made higher than that in the first method employing a silica sol.

In the hydrothermal treatment, an alkali metal salt is permitted to coexist with the silica hydrogel, and the pH of the treatment liquid is adjusted to an alkaline side, so that the silica solubility is increased to a proper level, and the crystallization speed due to so-called Ostwald aging, is increased, thereby to accelerate the conversion of the silica hydrogel to silica-X or the like. Here, the alkali metal salt may, for example, be an alkali metal hydroxide, an alkali metal silicate or an alkali metal carbonate. As the alkali metal, Li, Na or K is preferred. The pH of the system is preferably at least 7, more preferably from 8 to 13, most preferably from 9 to 12.5.

If a preferred amount of alkali is represented by a molar ratio of silica/alkali ($SiO_2/Me_2O$), it is preferably within a range of from 4 to 15 mol/mol, more preferably from 7 to 13 mol/mol. As mentioned above, the silica represents the total silica in the treatment liquid in the system and represents a value having silica taken into the system by sodium silicate or the like added to the silica of the silica hydrogel.

The hydrothermal treatment is carried out within a temperature range of from 150 to 220° C., preferably from 160 to 200° C., more preferably from 170 to 195° C.

If the temperature is substantially lower than the above range, it will take a long time to obtain the desired silica agglomerates. On the other hand, if it is substantially higher than the above range, the desired silica agglomerates tend to hardly be obtainable as a single phase of silica-X or silica-Y, such being undesirable. As mentioned above, silica-X or the like is considered to be an intermediate phase or a metastable phase, and it tends to undergo phase transfer to cristobalite or quartz as the hydrothermal treatment proceeds. Whereas, at a high temperature, particularly in a case where the temperature exceed 220° C., the crystallizing effect tends to increase, whereby a mixture of cristobalite and quartz tends to be obtained, or the crystallization reaction is so fast that it can not be controlled, whereby all undergoes a change into cristobalite or quartz.

Further, the time required for the hydrothermal treatment varies depending upon the temperature for the hydrothermal treatment or addition or non-addition of seed crystals. However, it is usually from 5 to 50 hours, preferably from 5 to 40 hours, more preferably from 5 to 15 hours, and most preferably from 6 to 12 hours, as in the case of the first method.

Further, in order to let the hydrothermal treatment proceed efficiently and to shorten the treating time, it is preferred to add seed crystals in an amount of from about 0.001 to 1 wt %, relative to the charged amount of the starting material silica hydrogel, although such addition is not essential. As the seed crystals, like in the first method, silica-X or silica-Y may be used as it is or after pulverization as the case requires. According to the study by the present inventors, when no seed crystals are added, or when silica-Y is used as seed crystals, silica agglomerates composed of silica-Y are likely to be formed, and when silica-X is used as seed crystals, agglomerates of silica-X are likely to be formed.

After completion of the hydrothermal treatment, the treated product is taken out of the autoclave and subjected to filtration and washing with water to adjust the pH, in the same manner as the first method.

The cake as the hydrothermally treated product obtained by the first method of treating a silica sol by hydrothermal treatment or the second method of treating a silica hydrogel by hydrothermal treatment, as described in the foregoing, is subjected to filtration and washing with water and observed in that state by a microscope, whereby formation of silica agglomerates (secondary particles) is observed wherein individual scaly primary particles are stacked and fused one on another. Namely, it is considered that majority of scaly silica primary particles obtained by such a method undergoes fusion of particles to one another and random stacking one on another to form silica agglomerates as secondary particles, during the process of crystal growth. Such agglomerates are characterized in that they have numerous voids formed by such random stacking of scaly silica.

Further, when such silica primary particles are inspected by a transmission electron microscopic (TEM) photograph, they are clearly observed to be scaly.

To use such agglomerates for the purpose of the present invention, it is preferred to dry them without dispersion treatment (pulverization treatment) i.e. an operation to disintegrate such agglomerates into primary particles.

The drying operation is carried out as they are or after washing them with a low boiling point organic solvent such as acetone or methanol to substitute attached water by the solvent. The drying apparatus is not particularly limited, and an optional apparatus such as a flash dryer, a fluidized bed dryer, a medium fluidized bed dryer, a stirring-type dryer, a cylindrical dryer, a tray dryer, a band dryer, a hot air dryer, a vacuum dryer, a vibration dryer or a spray dryer, may be employed. Further, the drying is preferably carried out usually at a temperature of from 50 to 300° C.

Figure 2:
FIG. 2 is a scanning electron microscopic photograph showing the particle structures of silica agglomerates.

FIGS. 1 and 2 are scanning electron microscopic (SEM) photographs showing silica agglomerates thus obtained, whereby it is clearly observed that scaly silica primary particles are randomly stacked to form silica agglomerates wherein numerous voids (spaces or pockets) formed by the stacking, are present. On appearance, the agglomerates may take various forms which may be variously expressed, such as, a cabbage-form, an onion-form, a petaloid form, a bud-form, a spiral shell-form, etc.

FIG. 1 is one obtained by the first method of treating a silica sol by hydrothermal treatment, and FIG. 2 is one obtained by the second method of treating a silica hydrogel by hydrothermal treatment. In either method, agglomerates having substantially the same shape can be obtained.

It can be regarded as unexpected that in the preferred second method wherein silica hydrogel particles are used as the starting material silica for hydrothermal treatment, silica agglomerates having a far smaller particle size (at a level of a few μm) are formed from the silica hydrogel which is spherical particles having a uniform particle size of from 2 to 6 mm, being transparent and having resiliency. Probably, such silica hydrogel particles are agglomerates of numerous silica primary particles having a particle size of a few nm which can never be distinguished by naked eyes, and during the hydrothermal treatment, a Si—O—Si bond, a hydrogen bond and a bond by precipitated silica, which are believed to bond and crosslink the primary particles to one another to form the secondary agglomerates (gel), may be readily broken, and the particles may be chemically dissociated and separated into individual silica primary particles. Such separated silica primary particles are believed to serve as the starting material to smoothly form low crystalline scaly silica primary particles of silica-X or silica-Y by the thermal treatment.

Whereas, in a case where a silica gel (silica xerogel) is used as the starting material as in the conventional method for producing silica-X or silica-Y, the situation is totally different. According to the study by the present inventors, even if silica gel particles are charged as they are into an autoclave, followed by hydrothermal treatment, the reaction does not substantially proceed, and the introduced silica gel stays as it is and no apparent change is observed. A silica gel is common to a silica hydrogel in that it is a gel formed by bonding and crosslinking of silica primary particles, but its bond is far strong that the chemical dissociation may not substantially occur during the hydrothermal treatment.

Accordingly, in the conventional method of using a silica gel as the starting material, it was necessary to preliminarily sufficiently pulverize the silica gel to fine particles of from 10 to 100 μm. Yet, even when such a mechanically pulverized silica gel is employed, in the conventional method, it took a long period of time for the hydrothermal treatment which can hardly be industrially acceptable.

When the silica hydrogel of the present invention is used, it is unnecessary to carry out mechanical pulverization. Probably, due to the presence of water in the gel, bonding among the primary particles is extremely weak, whereby the gel can readily be chemically dissociated to the individual primary particles during the hydrothermal treatment. The formed silica primary particles have a high reactivity by virtue of such a fine particle size (a few nm), and the solubility dependent on the particle size is also large, whereby Ostwald aging can be smoothly carried out, and the desired scaly silica primary particles are believed to form at a high temperature in a short period of time.

In the silica agglomerates of the present invention, scaly silica primary particles being randomly stacked, means not only a case where the surfaces of two scaly particles are completely stacked, but also stacking in various spatial relationships, such as stacking as between a part of a surface and a part of a surface, a surface and an edge, and an edge and an edge, whereby various forms of voids will be formed. Further, it is also conceivable that on the surfaces of the agglomerates thus formed, individual scaly silica particles are further stacked and fused to form new voids and to form larger agglomerates.

In the present invention, metal oxide particulates are supported on the surfaces of the silica agglomerates thus formed from scaly silica primary particles. The operation for this supporting can readily be carried out by adding and mixing metal oxide particulates to the silica agglomerates.

The mixing is carried out by a solid mixer which is commonly used. For example, a container-rotating type mixer such as a cylindrical mixer, a conical mixer, a V-type mixer, a Y-type mixer, a double conical mixer or a cubic type mixer; a container-fixed inner stirring type (inner rotary vane type) mixer such as a ribbon mixer, a screw mixer, a spade mixer, a Müller mixer, a single rotor mixer or a double rotor mixer; or a container-rotating inner stirring type mixer such as a reverse rotational Müfller mixer, may be suitably used. Further, it may be a mixer of a type where the container is shaked. Further, in the case of a container-rotating type mixer, it is sometimes preferred to put aluminum balls or steel balls together with the material to be mixed, in order to give a stronger shearing force to prevent agglomeration of fine particles to one another and to increase the mixing speed.

The mixing time may vary depending upon the type of the mixer used, the particle sizes, shapes, densities, charged amounts, wetted degrees and the desired mixing degrees, of the silica agglomerates and the metal oxide particulates, to be treated. However, it is usually from 5 minutes to 10 hours, preferably from 10 minutes to 5 hours.

In the present invention, the mixing treatment consists basically of adding and mixing dried metal oxide particulates to dried silica agglomerates, but is not necessarily limited thereto. For example, a wet cake composed of silica agglomerates, as the hydrothermally treated product, may be used without drying, and the metal oxide particulates may be added thereto, followed by mixing treatment. In a case where a wet cake is used, it is preferred to use a so-called blender, such as a kneader mixer, a pony mixer, a Müller mixer, an internal mixer or a roll mill. It is further preferred to use a blender equipped with a drying apparatus, so that mixing and drying can simultaneously be carried out. As the metal oxide particulates, those in a sol type highly dispersed in a suitable liquid medium in order to prevent agglomeration, are commercially available. In such a case, it is also preferred to use a mixing machine of a blender type.

Further, in some cases, the metal oxide particulates may be added to a slurry of silica agglomerates obtained by hydrothermal treatment, before filtration, so that the operation for adding and mixing treatment can be carried out in the solution. Otherwise, it is possible to employ a method wherein the metal oxide particulates themselves are formed by a reaction in a slurry of the silica agglomerates, so that highly active particulates just formed, may be adsorbed or deposited on the surfaces of the silica agglomerates, or may be grown on the surfaces. When such a mixing method is employed, the above-mentioned mechanical mixing of pulverization means may be applied before and/or after the filtration, as the case requires.

Figure 3:
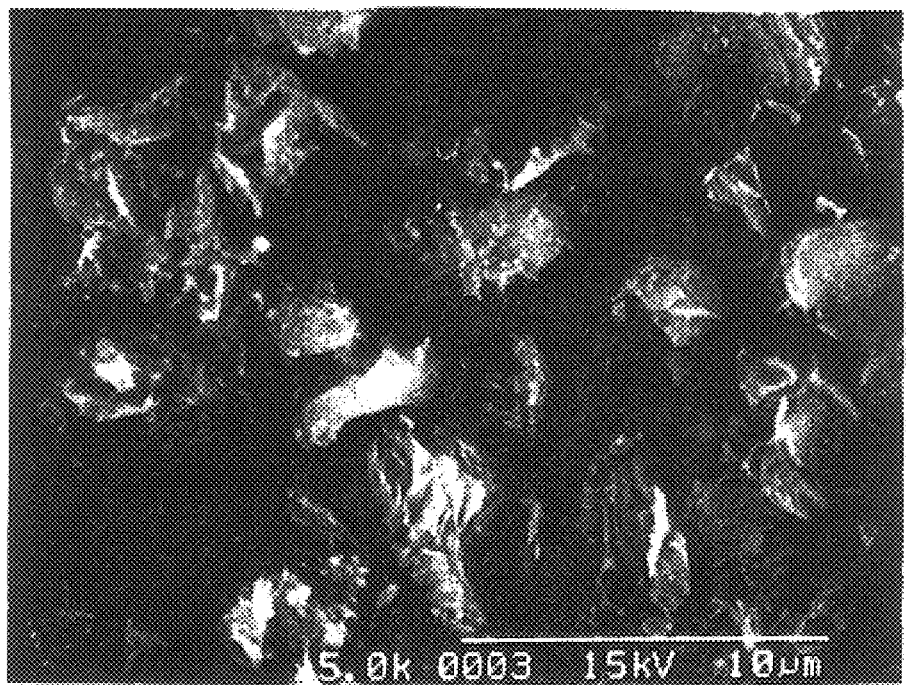
FIG. 3 is a scanning electron microscopic photograph showing the particle structures of a silica-metal oxide particulate composite.

FIG. 3 is a SEM photograph of a mixture obtained by mixing 16 parts by weight of titanium dioxide particulates to 84 parts by weight of the silica agglomerates shown in FIG. 1 for 30 minutes.

Figure 4:
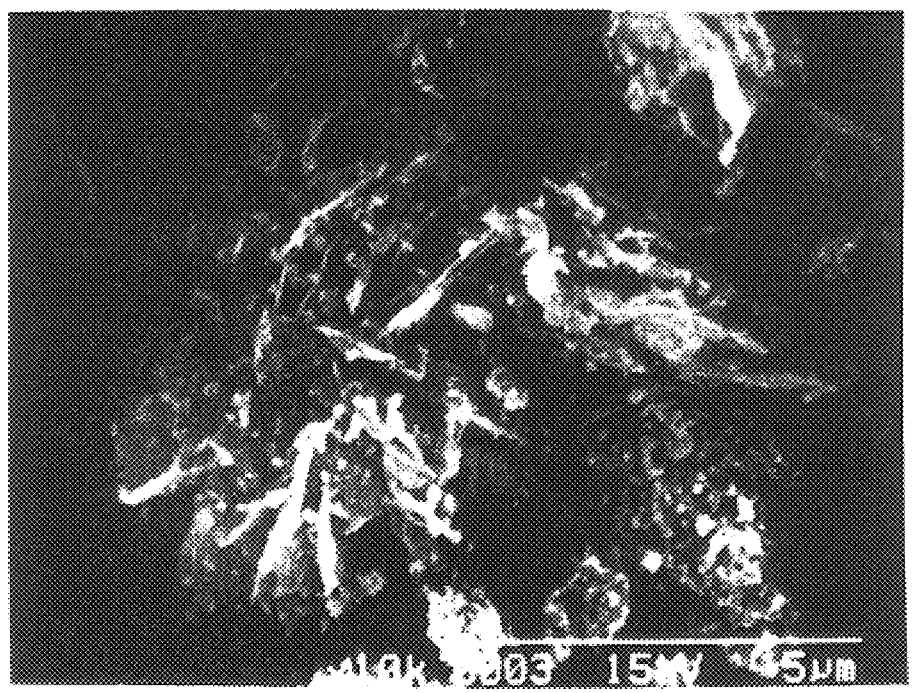
FIG. 4 is a scanning electron microscopic photograph showing the particle structures of a silica-metal oxide particulate composite.

It is observed that titanium dioxide particulates are supported in a dispersed state on the surfaces of the silica agglomerates, and substantially no titanium dioxide particles are observed which are in a free state as departed from the surfaces. Further, the magnification of SEM has been increased to study the details, whereby it has been confirmed, for example, as shown in FIG. 4 that many titanium dioxide particulates are located in voids (spaces or pockets) formed by random stacking of scaly silica, and they exist in a state as captured in the voids and as supported on the inner surfaces (i.e. the inner wall surfaces) in the voids. Namely, it is evident that the voids in the silica agglomerates used in the present invention serve as a sort of pockets which capture and support the metal oxide particulates such as titanium dioxide particulates.

Whereas, in a case where silica particles of other shapes such as a spherical shape, are used, it is impossible to form a composite having the incorporated metal oxide particulates supported on the surface in such a manner.

Figure 5:
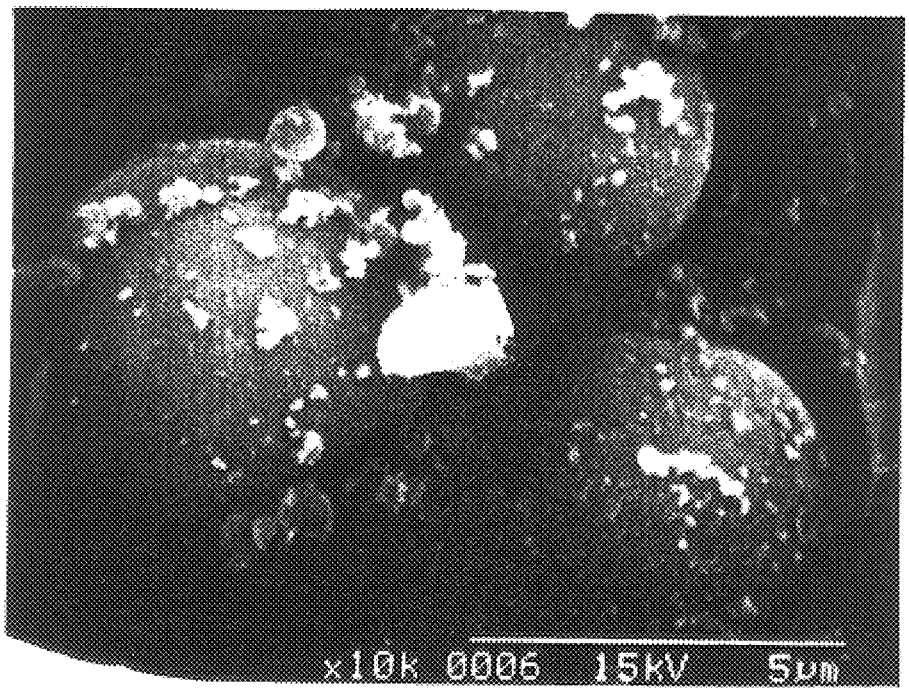
FIG. 5 is a scanning electron microscopic photograph showing the particle structures wherein metal oxide particulates are distributed on silica spherical particles.

FIG. 5 is a SEM photograph showing a result when titanium dioxide particulates were blended in the same proportion as in the case of FIG. 3 to spherical silica particles having a particle size substantially equal to the silica agglomerates, followed by mixing treatment. As is different from the case of the present invention in which agglomerates composed of scaly silica particles, are used, it is observed that most titanium dioxide particulates are freed from the surfaces of the silica particles or are agglomerated themselves, and they are not supported in a dispersed state on the spherical silica surfaces. Namely, when the mixture of the spherical silica particles and the titanium dioxide particulates, is observed microscopically, the respective particles are spatially separately present, and as a whole, such can not be regarded as a silica composite as in the present invention.

The difference between the two is more distinctly demonstrated by an experiment in which a dispersing medium such as water is added to a sample of particles shown in each of FIGS. 3 and 5, followed by shaking and leaving to stand still.

Namely, in the case of the silica-metal oxide particulate composite of the present invention shown in FIG. 3, the composite settles in a short time, and the supernatant becomes clear. This means that the metal oxide particulates settle as supported on the composite and they are scarcely separated from the composite and released in water. Whereas, in the case of the blend of the metal oxide particulates into spherical silica as shown in FIG. 5, the situation is totally different, and it is clearly observed that only the silica particles settle, and the supernatant is colored and turbidified as a large amount of separated metal oxide particulates float and are dispersed therein. This also proves that in the spherical silica blend, the blended metal oxide particulates are not in the supported state in terms of the present invention.

Thus, in the silica-metal oxide particulate composite of the present invention, the metal oxide particulates are in such a state as supported on the surfaces, and the inner surfaces in the voids, of the silica agglomerates, as observed from the SEM photographs and the above experiment. Here, "supported" means that by the van der Waals force, an electrostatic force or any other optional force, the metal oxide particulates are fixed as attached, adsorbed or bonded to the surfaces of the silica agglomerates.

The silica agglomerates used in the present invention, have numerous voids (spaces or pockets) formed by random stacking of the scaly silica, whereby the surfaces and the inner surfaces in the voids serve as supporting sites for the material to be supported. Accordingly, the silica agglomerates themselves are useful as a carrier for organic/inorganic fungicides or as a carrier for culturing cells.

The silica-metal oxide particulate composite of the present invention (i) has excellent ultraviolet ray-shielding performance and yet (ii) provides an unexpected effect such that the decomposition or deterioration of an organic compound due to a photocatalytic oxidation action is less or at most equal to the one having metal oxide particulates included and complexed in silica particles, as shown in the Examples given hereinafter. This mechanism can not be clearly understood at the present stage, but is assumed to be as follows.

Firstly, with respect to (i), the silica agglomerates used as the matrix in the present invention have a wide outer surface area, as the shape of the primary particles as constituting units is scaly, while the metal oxide particulates added thereto have a particle size which is very fine as compared with the scaly silica, and their surfaces are highly active as they are fine particles. Accordingly, in the process of mechanical mixing, they are strongly adsorbed on the outer surfaces of the scaly silica and form thin adsorbed layers (including not only continuous layers but also dispersed or separated layers) on the front and rear surfaces thereof. The metal oxide particulates thus once adsorbed and fixed to the surfaces of the scaly silica (i.e. the surfaces of the silica agglomerates) will no longer readily be released from the surfaces and securely supported on the surfaces. Further, the silica agglomerates have numerous voids formed by random stacking of scaly silica primary particles, and the metal oxide particulates are considered to be captured in the voids and likewise form adsorbed layers also on the inner surfaces in the voids.

Namely, the surfaces, and the inner surfaces in the voids, of the silica agglomerates may be regarded as surface-modified over the entire surface by the adsorbed metal oxide particulates. Thus, the metal oxide particulates mixed and blended to the silica agglomerates, are stably dispersed and supported along the surfaces of the silica agglomerates, whereby it is substantially unlikely that the metal oxide particulates are present in a free state or the particulates are agglomerated by themselves. As will be readily understood, this supported state is the most preferred spatial state for the metal oxide particulates to perform e.g. the ultraviolet ray-shielding function. Taking this into consideration, it can be said natural that the composite of the present invention has an excellent ultraviolet ray-shielding function.

Further, with respect to (ii), during the mechanical mixing in a mixer, especially when stirring vanes or alumina balls, etc., are present in the mixer, the silica agglomerates made of scaly silica will receive substantial impact and shear forces, and especially breakable portions, such as end portions, corner portions or edge portions of scales, will break to form numerous very fine silica powder particles, which will be separated from the parent silica agglomerates. Such fine silica powder particles have newly formed cut surfaces, and the chemical potential of such surfaces is in an extremely high state (mechanical activity). This is believed to provide a driving force, and a substantial portion of the fine silica powder particles is considered to be adsorbed on the surfaces of the nearby metal oxide particulates. Namely, it is considered that the surfaces of the metal oxide particulates are covered by the newly formed fine silica powder particles. Accordingly, it may be that in reality, the surfaces of the metal oxide particulates which are exposed, are smaller than anticipated.

The silica agglomerates obtained by any one of the above-described methods proposed by the present inventor, has the following properties, and accordingly, it is particularly preferred that they are used for incorporation to cosmetics.

Namely, such silica agglomerates are composed of scaly silica having an extremely low crystallinity such that the measured value of free silicic acid of crystal type which is believed to cause silicosis, is less than 10%, preferably less than 5%, more preferably less than 2% (below the detectable limit), as measured by the X-ray diffraction analysis described in Guidebook for Measuring Working Environment (Related to Mineral Dust, compiled by the Ministry of Labor, Safety and Hygiene Department, Environmental Improvement Section) in accordance with Working Environment Measuring Standard shown in a notification relating to Labor Safety and Hygiene Law, and thus they are believed to be sufficiently safe to human bodies.

Such silica-metal oxide particulate composite of the present invention has various applications. For example, when the metal oxide particulates have an ultraviolet-shielding function, the composite may be incorporated as an ultraviolet ray-shielding agent to cosmetics, coating materials or resins.

The cosmetics to which the composite may be incorporated, may be those which are commonly produced, such as foundations, milky lotions, other lotions, creams, pastes, sticks, lip sticks, rouges, eye shadows, body powders, eyebrow pencils, eyeliners, mascaras, face powders, antiperspirants, shampoos, rinses or mousses.

Such cosmetics may contain an oily or fatty substance such as vaseline, liquid paraffin, lanolin, wax or a fatty acid ester, an organic solvent such as ethanol, isopropanol or glycerol, an emulsifier such as triethanolamine, and other cosmetic adjuvants which are commonly used for cosmetics, such as silicone, a thickener, a perfume, a preservative, an antiseptic, a surfactant, a metal ion sealing agent, a dye, a pH regulating agent or a moisturizing agent.

In a case where the silica-metal oxide particulate composite of the present invention is to be incorporated to a resin, the resin may, for example, be a vinyl chloride resin, a vinylidene chloride resin, polyethylene, polypropylene, polystyrene, an ABS resin, polycarbonate, nylon, a polyacetal resin, a polyamide resin, a polyimide resin, a melamine resin, a silicone resin, an acrylic resin, a metacrylic resin, a phenol resin, a polyester resin, a urea resin or a fluorine resin.

Further, in the case where it is to be incorporated to a coating material, the resin for a coating material may, for example, be a polyvinyl alcohol resin, a vinyl chloride/vinyl acetate resin, an acrylic resin, an epoxy resin, an alkyd resin, a polyester resin, a urethane resin, a polyamide resin, a polyimide resin, a phenol resin or an amino resin, which may be dispersed in water or an organic solvent to form a coating material.

When incorporated to a cosmetic, a resin, a coating materiel or the like, the surface of the particles of the fine particulate composite of the present invention may be surface-treated with silicone oil, a silane coupling agent, a titanate coupling agent, an alcohol, a surfactant, or other surface treating agent or surface modifier. When one so-treated to make the surface hydrophobic, is incorporated to a cosmetic, the cosmetic will have a long lasting effect. Further, when one treated with a coupling agent is incorporated to a resin, the strength will be improved, and the dispersion stability will increase.

The metal oxide particulates are useful for a fungicide, an EL element, a photoelectric element, a semiconductor element or a non-linear element in addition to a case having a function as a shielding material against lights with a certain wavelength such as an ultraviolet ray-shielding function. Accordingly, the silica-metal oxide particulate composite of the present invention is useful also in such a field.

Further, in the silica-metal oxide particulate composite of the present invention, the following particulates may be used in place of the metal oxide particulates.

Namely, particulates of a metal such as gold, silver, platinum, copper or aluminum, or its alloy; particulates of a sulfide or sulfate such as cadmium sulfide, zinc sulfide, antimony sulfide, lead sulfide, nickel sulfide, strontium sulfate or barium sulfate; particulates of a phosphate such as copper pyrophosphate; particulates of a carbide, such as tantalum carbide, zirconium carbide, tungsten carbide, vanadium carbide, titanium carbide or silicon carbide, or particulates of a halide such as calcium fluoride. The copper pyrophosphate particulates are useful as a material having an infrared-shielding function.

Now, specific embodiments of the present invention will be described with reference to Examples. However, it should be understood that the present invention is by no means restricted to such specific Examples.

In the following Examples, as an apparatus for hydrothermal treatment, an autoclave having a capacity of 5,000 cm$^3$ (an electric heating system, equipped with anchor-type stirring vanes) was used.

The aspect ratio of silica agglomerates was obtained by measuring the thickness, the maximum length and the minimum length, by means of e.g. a scale, with respect to a sufficiently large number of images of scaly primary particles photographed by a scanning electron microscope.

EXAMPLE 1

Into an autoclave (electric heating type, provided with anchor-type stirring vanes), 2,183 g of active silicic acid (composition: 9.16 wt % of $SiO_2$ and 1.35 wt % of $Na_2O$, $SiO_2/Na_2O=7.0$ mol/mol) and 1,817 g of deionized water were charged, and 0.5 g of seed crystals were added, and then hydrothermal treatment was carried out at 200° C. for 8.5 hours with stirring at 200 rpm.

The active silicic acid as starting material, was one obtained by diluting water glass of JIS No. 3 with water, followed by electrodialysis, and wherein the average particle size of colloidal silica was at most 3 nm as measured by a laser scattering particle size measuring apparatus, manufactured by Otsuka Denshi K.K.

The hydrothermally treated product was subjected to filtration and washing with water, followed by drying by means of a medium fluidized bed dryer to obtain 151 g of a fine powder. With respect to the formed fine powder, the formed phase was identified by the powder X-ray diffraction spectrum, whereby it was found to be a single phase of silica-X characterized by peaks at 2θ=4.9° and 26.0°. Further, the oil absorption (JIS K5101) of the fine powder was measured and found to be 105 ml/100 g.

The shape of the product was observed by SEM, whereby the shapes of the primary particles were found to be scaly, and such scaly primary particles were observed as randomly stacked to form silica agglomerates having voids. The average thickness of the scaly primary particles was 0.05 $\mu$m, and the average maximum length of scales was 3 $\mu$m. Accordingly, the aspect ratio of the average maximum length to the average thickness was 60. The average minimum length of the scales was 1.2 $\mu$m, and the aspect ratio of the average minimum length to the average thickness was accordingly 24.

Further, the amount of free crystalline silicic acid in the fine powder was measured by an X-ray diffraction analysis and found to be less than the detectable limit (less than 2%).

Then, the above silica agglomerates and titanium dioxide particulates (TTO-55A, tradename, manufactured by Ishihara Sangyo K.K., average particle size: 0.03 to 0.05 $\mu$m) were sampled so that the total weight of the two would be 5.0 g, and the weight ratio of silica: titanium dioxide=84 wt %:16 wt %, put into a shaking type powder mixer (Turbler Shaker Mixer T2C Model, tradename, capacity: 100 cm$^3$, containing aluminum balls) manufactured by Kabushiki Kaisha Shinmaru Enterprises, and mixed for 30 minutes.

Figure 6:
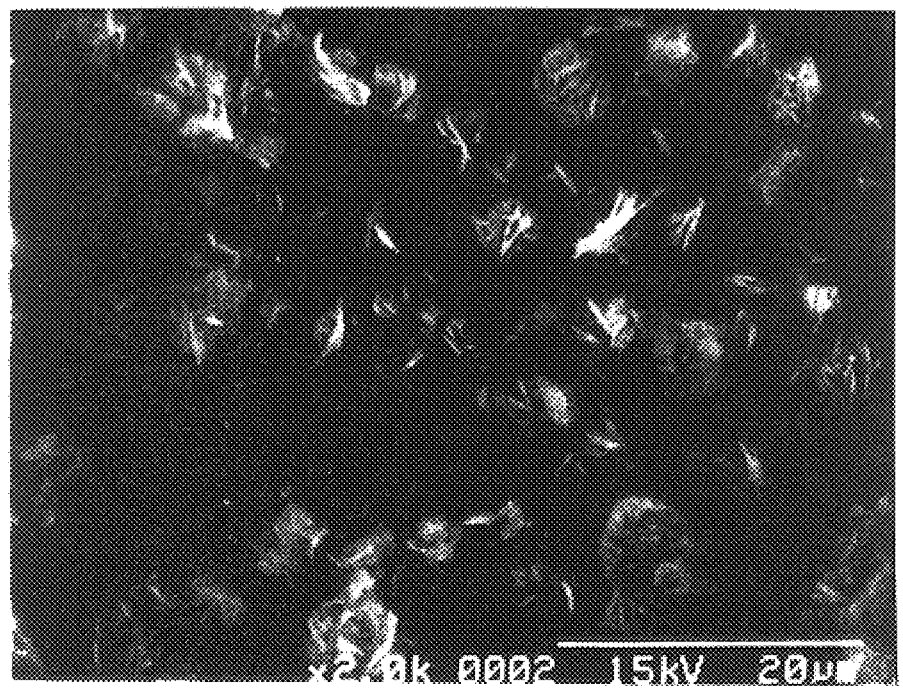
FIG. 6 is a scanning electron microscopic photograph showing the particle structures of a silica-metal oxide particulate composite.
Figure 7:
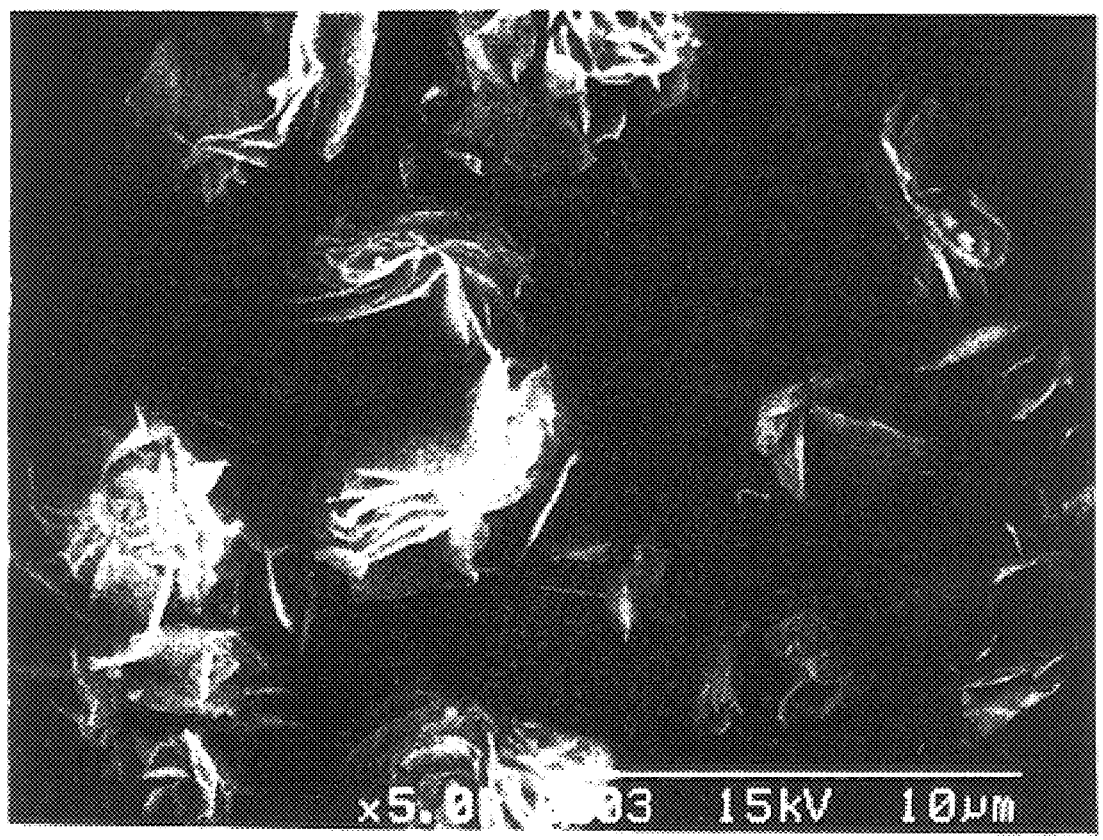
FIG. 7 is a scanning electron microscopic photograph showing the particle structures of a silica-metal oxide particulate composite.

The fine powder after mixing (the silica composite of the present invention) was observed by SEM, whereby it was found that titanium dioxide particulates were supported as very uniformly dispersed on the surfaces, and on the inner surfaces in voids, of the silica agglomerates. Further, it was found the silica agglomerates maintained substantially the initial shape without being substantially pulverized or disintegrated so as to be confirmed with naked eyes. FIGS. 6 and 7 show examples of SEM photographs with different magnifications of the agglomerates thus obtained.

Then, 1.12 g of vaseline and 0.48 g of the liquid paraffin were added to 0.4 g of the fine powder and thoroughly dispersed by means of a three-roll mill to obtain a paste. The paste was sandwiched between a pair of quartz plates having a thickness of 2 mm and spreaded until the layer thickness became 25 $\mu$m, whereupon the spectral transmittance was measured by means of an automatic spectrophotometer. The transmittances at various wavelengths are shown in Table 1. A wavelength beyond 400 nm represents the visible light region, and a wavelength within a range of from 280 to 400 nm represents the ultraviolet region. The smaller the transmittance in the ultraviolet region, the better the ultraviolet ray-shielding effect. The larger the transmittance in the visible light region, the higher the transparency as observed with naked eyes. At 500 nm, the transmittance was 63.51%, at 400 nm, the transmittance was 48.63%, at 360 nm, the transmittance was 16.81%, at 320 nm, the transmittance was 7.57%, and at 290 nm, the transmittance was 8.03%. Further, as compared with Comparative Example 1 given hereinafter, it is evident that the transmittance in the ultraviolet region can be made lower than the case where the matrix silica is a fine spherical silica gel.

Further, with respect to the decomposition characteristic of an organic substance by a photocatalyst of the metal oxide particles, 25 ml of isopropyl alcohol was put into a 50 ml transparent glass bottle, and 1.09 g (containing 0.175 g of $TiO_2$) of the above mixed fine powder was added thereto, whereupon the bottle was sealed and exposed to the direct sunlight for 8 hours with stirring by a stirrer. Then, the amount of acetone formed by decomposition of the isopropyl alcohol by the photocatalytic oxidation action, was measured by gas chromatography, and the result was shown in Table 3. As shown, the acetone amount was 0.06 vol %. This amount was found to be sufficiently low even when compared with the value (0.13%) in Comparative Example 7 given hereinafter in which titanium dioxide was incorporated and dispersed in the silica gel particles.

EXAMPLE 2

Using the same silica agglomerates as in Example 1, a composite was formed so that the blend ratio of the silica agglomerates to the titanium dioxide particulates would be a weight ratio of silica:titanium dioxide particulates=64 wt %:36 wt %, and similar tests were carried out. The results are shown in Tables 1 and 3.

As is apparent from Table 1, the transmittance of the composite in the visible light region was fairly low, but the transmittance in the ultraviolet region was particularly low.

EXAMPLE 3

Using the same silica agglomerates as in Example 1, a composite was formed so that the blend ratio of the silica agglomerates to the titanium dioxide particulates would be a weight ratio of silica:titanium dioxide particulates=92 wt %:8 wt %, and similar tests were carried out. The results are shown in Tables 1 and 3.

EXAMPLE 4

The same tests as in Example 1 were carried out except that the titanium dioxide particulates were changed to zinc oxide particulates. As the zinc oxide, zinc oxide particulates (ZnO-310, tradename, average particle size: 0.03 $\mu$m) manufactured by Sumitomo Osaka Cement K.K. were used, and the blend ratio of the silica to the zinc oxide particulates was adjusted to a weight ratio of the silica agglomerates:the zinc oxide particulates=84 wt %:16 wt %. A composite was formed in the same manner as in Example 1 except for the above conditions, and tests were carried out under the same conditions. The test results are shown in Tables 1 and 3. As is apparent from Table 1, the transmittance of the composite in the visible light region was fairly high, and yet, the transmittance in the ultraviolet region was low.

Further, as compared with Comparative Example 4 wherein a fine spherical silica gel was used as the matrix silica, it is evident that with the composite of the present invention, the transmittance in the ultraviolet region can be made substantially low.

EXAMPLE 5

Tests similar to Example 4 were carried out under the condition such that only the blend ratio of the silica agglomerates to the zinc oxide particulates was changed to a weight ratio of the silica:the zinc oxide particulates=64 wt %:36 wt %, and the results are shown in Tables 1 and 3.

It is evident that this composite exhibits a characteristic such that the transmittance in the visible light region is high, and the transmittance in the ultraviolet region is low.

EXAMPLE 6

Tests similar to Example 4 were carried out under the condition such that only the blend ratio of the silica agglomerates to the zinc oxide particulates was changed to a weight ratio of the silica agglomerates:the zinc oxide particulates= 92 wt %:8 wt %, and the results are shown in Tables 1 and 3.

This composite exhibited a characteristic such that the transmittance in the visible light region is particularly high, and the transmittance in the ultraviolet region is not so low.

EXAMPLE 7

Using the same silica agglomerates as in Example 1, both titanium dioxide particulates and zinc oxide particulates were blended, and tests were carried out.

The same silica agglomerates as in Example 1, titanium dioxide particulates (TTO-55A, tradename, average particle size: 0.03 to 0.05 μm) manufactured by Ishihara Sangyo K.K. and zinc oxide particulates (ZnO-310, tradename, average particle size: 0.03 μm) manufactured by Sumitomo Osaka Cement K.K. were sampled so that the total amount of the three materials would be 5.0 g, and the weight ratio of silica:titanium dioxide:zinc oxide=76 wt %:12 wt %:12 wt %, and tests were carried out under the same conditions as in Example 1. The test results are shown in Table 2.

As is evident from Table 2, the obtained composite exhibited a characteristic that it simultaneously has preferred properties such that the transmittance in the visible light region is high, and yet, the transmittance in the ultraviolet region is fairly low.

EXAMPLE 8

Tests similar to Example 7 were carried out under the condition such that only the blend ratio of silica to titanium dioxide and zinc oxide, was changed to a weight ratio of silica:titanium dioxide:zinc oxide=84 wt %:8 wt %:8 wt %, and the results are shown in Table 2.

EXAMPLE 9

Tests similar to Example 7 were carried out under the condition such that only the blend ratio of silica to titanium dioxide and zinc oxide, was changed to a weight ratio of silica:titanium dioxide:zinc oxide=90 wt %:5 wt %:5 wt %, and the results are shown in Table 2.

EXAMPLE 10

Using the same silica agglomerates as in Example 1, both of titanium dioxide particulates and zinc oxide particulates were blended, and tests were carried out.

The same silica agglomerates as in Example 1, titanium dioxide particulates (TTO-55A, tradename, average particle size: 0.03 to 0.05 μm) manufactured by Ishihara Sangyo K.K. and zinc oxide particulates (Fine Zinc White, tradename, average particle size: 0.3 μm) manufactured by Honjo Chemical K.K. were sampled so that the total weight would be 5.0 g, and the weight ratio of silica:titanium dioxide:zinc oxide=76 wt %:12 wt %:12 wt %, and tests were carried out under the same conditions as in Example 1. The test results are shown in Table 2.

From the Table, it is evident that the obtained composite exhibits a characteristic that it simultaneously has properties such that the transmittance in the visible light region is high, and yet the transmittance in the ultraviolet region is fairly low.

EXAMPLE 11

Tests similar to Example 10 were carried out under the condition such that only the blend ratio of silica to titanium dioxide and zinc oxide, was changed to a weight ratio of silica:titanium dioxide:zinc oxide=84 wt %:8 wt %:8 wt %, and the results are shown in Table 2.

EXAMPLE 12

Tests similar to Example 7 were carried out under the condition such that only the blend ratio of silica to titanium dioxide and zinc oxide, was changed to a weight ratio of silica:titanium dioxide:zinc oxide=90 wt %:5 wt %:5 wt %, and the results are shown in Table 2.

EXAMPLE 13

Using the same powder as in Example 1, tests were carried out under the same conditions as in Example 1 except that as a mixing method of the silica agglomerates and the titanium oxide particulates, only the powders to be mixed were put into a shaking type powder mixer (a mixing container (capacity 100 cm$^3$) of Turbler Shaker Mixer T2C Model, tradename) manufactured by Kabushiki Kaisha Shinmaru Enterprises without putting alumina balls, and shaked and mixed for 30 minutes.

The results of measurement of the spectral transmittance by the automatic spectrophotometer were such that at a wavelength of 500 nm, the transmittance was 70.39%, at 400 nm, the transmittance was 55.05%, at 360 nm, the transmittance was 21.17%, at 320 nm, the transmittance was 9.05%, and at 290 nm, the transmittance was 10.25%.

EXAMPLE 14

Into an autoclave (electric heating type, provided with anchor-type stirring vanes), 2,183 g of active silicic acid (composition: 9.16 wt % of $SiO_2$ and 1.35 wt % of $Na_2O$, $SiO_2/Na_2O$=7.0 mol/mol) and 1,817 g of deionized water were charged, and 0.5 g of seed crystals were added thereto, whereupon hydrothermal treatment was carried out at 190° C. for 16 hours with stirring at 200 rpm.

The active silicic acid as starting material was one obtained by diluting water glass of JIS No. 3 with water, followed by electrodialysis, and the average particle size of colloidal silica therein was at most 3 nm as measured by a laser scattering particle size measuring apparatus, manufactured by Otsuka Denshi K.K.

The hydrothermally treated product was subjected to filtration and washing with water, followed by drying by means of a medium fluidized bed dryer, to obtain 155 g of a fine powder.

With respect to the formed fine powder, the formed phase was identified by the powder X-ray diffraction spectrum. As the X-ray diffraction spectrum, in addition to the main peaks of silica-X characterized by the main peaks at 2θ=4.9° and 26.0° which correspond to No. 16-0380 of card registered at ASTM (American Society for Testing and Materials, hereinafter referred to simply as ASTM), U.S.A., (hereinafter referred to simply as ASTM Card), peaks corresponding to ASTM Card Nos. 37-0386 and 31-1234 were observed.

The shape of the product was observed by SEM, whereby the shapes of the primary particles were scaly, and it was observed that such scaly primary particles were randomly stacked to form silica agglomerates having voids. Further, the oil absorption (JIS K5101) of the fine powder was measured and found to be 103 ml/100 g.

The average thickness of the scaly silica primary particles was 0.05 μm, and the average maximum length of scales was 3 μm, and the aspect ratio of the average maximum length to the thickness was accordingly 60. The average minimum length of the scales was 1.5 μm, and the aspect ratio of the average minimum length to the thickness was accordingly 30.

Further, the amount of free crystalline silicic acid was measured by an X-ray diffraction analysis and was found to be less than the detectable limit (less than 2%).

Then, the above silica agglomerates and titanium dioxide particulates (TTO-55A, tradename, manufactured by Ishihara Sangyo K.K., average particle size: 0.03 to 0.05 μm) were sampled so that the total amount of the two would be 5.0 g, and the weight ratio of silica:titanium dioxide=84 wt %:16 wt %, put into a shaking type powder mixer manufactured by Kabushiki Kaisha Shinmaru Enterprises (Turbler Shaker Mixer T2C Model, tradename, capacity: 100 cm$^3$, containing aluminum balls) and mixed for 30 minutes.

The fine powder after mixing was observed by SEM, whereby it was found that titanium dioxide particulates were supported as very uniformly dispersed on the surfaces, and on the inner surfaces in the voids, of the silica agglomerates composed of scaly silica primary particles. Further, the silica agglomerates maintained substantially the initial shape.

Then, 1.12 g of vaseline and 0.48 g of liquid paraffin were added to 0.4 g of the mixed fine powder (the silica composite of the present invention) and thoroughly dispersed by means of a three-roll mill to obtain a paste. The paste was sandwiched between a pair of quartz plates having a thickness of 2 mm and spreaded until the layer thickness became 25 μm, whereupon the spectral transmittance was measured by means of an automatic spectrophotometer. The transmittances at various wavelengths are shown in Table 1. A wavelength beyond 400 nm represents the visible light range, and a wavelength within a range of from 280 to 400 nm represents the ultraviolet region. The smaller the transmittance in the ultraviolet region, the better the ultraviolet ray-shielding effect. The larger the transmittance in the visible light region, the higher the transparency as observed by naked eyes. At 500 nm, the transmittance was 62.23%, at 400 nm, the transmittance was 47.68%, at 360 nm, the transmittance was 16.50%, at 320 nm, the transmittance was 7.45%, and at 290 nm, the transmittance was 7.86%. This composite exhibited a characteristic such that the transmittance in the visible light region was low, but the transmittance in the ultraviolet region was very low.

Further, it is evident that with the silica-metal oxide particulate composite of the present invention, the transmittance in the ultraviolet region can be made lower than a case (Comparative Example 1) wherein the silica used as a matrix is a fine spherical silica gel.

Further, with respect to the decomposition characteristic of an organic substance by a photocatalyst of metal oxide particles, 25 ml of isopropyl alcohol was put into a 50 ml transparent glass bottle, and 1.09 g (containing 0.175 g of TiO$_2$) of this composite was added thereto. The bottle was sealed and exposed to direct sunlight for 8 hours, while stirring by a stirrer. Then, the amount of acetone formed by decomposition of isopropyl alcohol by a photocatalytic oxidation action, was measured by gas chromatography, and the result is shown in Table 3. The acetone amount was 0.07 vol %. This amount was found to be sufficiently low as compared with the numerical value (0.13%) in Comparative Example 7 given hereinafter wherein titanium dioxide was incorporated and dispersed in silica gel particles.

Further, for a confirmation purpose, the same study was carried out with respect to a composite wherein scaly silica having ASTM No. 37-0386, was used as the matrix, whereby substantially the same results were obtained.

Comparative Example 1

Fine spherical silica gel (Sunsphere H-31, tradename, average particle size: 3.0 μm, pore volume: 1.0 cm$^3$/g, average pore diameter: 60 Å) manufactured by Asahi Glass Company Ltd. and titanium dioxide particulates (TTO-55A, tradename, average particle size: 0.03 to 0.05 μm) manufactured by Ishihara Sangyo K.K., were sampled so that the total weight of the two would be 5.0 g, and the weight ratio of the fine spherical silica gel:the titanium dioxide would be 84 wt %:16 wt %, put into a shaking type powder mixer manufactured by Kabushiki Kaisha Shinmaru Enterprises (Turbler Shaker Mixer T2C Model powder mixer, tradename, capacity: 100 cm$^3$, containing alumina balls) and mixed for 30 minutes.

The fine powder after mixing was observed by SEM, whereby no pulverization of the fine spherical silica particles was observed. Further, as shown in FIG. 5, most titanium dioxide particulates were freed from the surfaces of silica particles or agglomerated by themselves, and thus it was observed that the dispersibility was very poor as compared with the case of Example 1 wherein the silica agglomerates were used. This fine powder was put into water, shaked and then left to stand still, whereby the supernatant was found to be turbid due to titanium dioxide particulates floating as separated from silica particles, as mentioned above.

Then, 1.12 g of vaseline and 0.48 g of liquid paraffin were added to 0.4 g of this mixed fine powder and thoroughly dispersed by means of a three-roll mill to obtain a paste. The paste was sandwiched between a pair of quartz plates having a thickness of 2 mm and spreaded until the layer thickness became 25 μm, whereupon the spectral transmittance was measured by means of an automatic spectrophotometer, and the results are shown in Table 4. A wavelength beyond 400 nm represents the visible light region, and a wavelength within a range of from 280 to 400 nm represents the ultraviolet region.

At 500 nm, the transmittance was 69.89%, at 400 nm, the transmittance was 55.67%, at 360 nm, the transmittance was 24.99%, at 320 nm, the transmittance was 11.20%, and at 290 nm, the transmittance was 12.02%.

Comparative Examples 2 to 6

Using the same fine spherical silica gel and titanium dioxide particulates as in Comparative Example 1 and zinc oxide particulates manufactured by Sumitomo Osaka Cement K.K. (ZnO-310, tradename, average particle size: 0.03 μm), tests were carried out in the same manner as in Example 1 except that the total amount of two was 5.0 g, and the ratio was as shown in Table 4. The results are shown in Table 4.

Comparative Example 7

With respect to a product of Dokai Kagaku Kogyo K.K. having titanium dioxide ultrafine particles having an average particle size of 0.03 μm incorporated and dispersed in fine spherical silica gel particles having a particle size of 3 μm (ratio of silica:titanium dioxide=65 wt %:35 wt %), the spectral transmittance was measured by an automatic spectrophotometer under the same conditions as in Example 1, and the results are shown in Table 5. On the other hand, the amount of acetone formed as a decomposition product of isopropyl alcohol by a photocatalytic action as measured under the same conditions as in Example 1 with respect to this spherical silica gel having titanium dioxide ultrafine particles incorporated, was 0.13 vol %.

Comparative Example 8

With respect to a product of Dokai Kagaku Kogyo K.K. having zinc oxide ultrafine particles having an average particle size of 0.3 μm incorporated and dispersed in the particles of fine spherical silica gel having a particle size of 3 μm (ratio of silica:zinc oxide=55 wt %:45 wt %, average particle size: 3 μm), the spectral transmittance was measured by an automatic spectrophotometer under the same conditions as in Example 1. The results of the measurements are shown in Table 5.

TABLE 1

| | Wavelength (nm) $SiO_2/TiO_2/ZnO$ | Transmittances (%) at various wavelengths | | | | |
|---|---|---|---|---|---|---|
| | weight ratio | 500 | 400 | 360 | 320 | 290 |
| Example 1 | 84/16/0 | 63.51 | 48.63 | 16.81 | 7.57 | 8.03 |
| Example 2 | 64/36/0 | 55.66 | 40.58 | 9.91 | 4.66 | 5.23 |
| Example 3 | 92/8/0 | 79.23 | 65.25 | 37.32 | 17.29 | 18.16 |
| Example 4 | 84/0/16 | 92.08 | 83.44 | 24.19 | 22.93 | 21.93 |
| Example 5 | 64/0/36 | 87.06 | 74.98 | 12.17 | 13.23 | 12.96 |
| Example 6 | 92/0/8 | 95.61 | 91.00 | 44.38 | 44.05 | 42.33 |
| Example 13 | 84/16/0 | 70.39 | 55.05 | 21.17 | 9.05 | 10.25 |
| Example 14 | 84/16/0 | 62.23 | 47.68 | 16.50 | 7.45 | 7.86 |

TABLE 2

| | Wavelength (nm) $SiO_2/TiO_2/ZnO$ | Transmittances (%) at various wavelengths | | | | |
|---|---|---|---|---|---|---|
| | weight ratio | 500 | 400 | 360 | 320 | 290 |
| Example 7 | 76/12/12 | 74.70 | 64.70 | 18.64 | 10.28 | 10.84 |
| Example 8 | 84/8/8 | 79.57 | 65.42 | 27.82 | 15.50 | 16.05 |
| Example 9 | 90/5/5 | 84.32 | 70.90 | 29.47 | 15.72 | 15.59 |
| Example 10 | 76/12/12 | 67.75 | 52.59 | 15.53 | 9.46 | 10.09 |
| Example 11 | 84/8/8 | 73.45 | 58.26 | 20.69 | 11.93 | 12.51 |
| Example 12 | 90/5/5 | 80.50 | 65.73 | 29.93 | 15.66 | 15.96 |

TABLE 3

| | $SiO_2/TiO_2/ZnO$ weight ratio | Amount of acetone formed from isopropyl alcohol by the photocatalytic oxidation decomposition action (vol %) |
|---|---|---|
| Example 1 | 84/16/0 | 0.06 |
| Example 2 | 64/36/0 | 0.10 |
| Example 3 | 92/8/0 | 0.04 |
| Example 4 | 84/0/16 | 0.03 |
| Example 5 | 64/0/36 | 0.03 |
| Example 6 | 92/0/8 | 0.03 |
| Example 14 | 84/16/0 | 0.07 |
| Comparative Example 7 | 65/35/0 | 0.13 |

TABLE 4

| | Wavelength (nm) $SiO_2/TiO_2/ZnO$ | Transmittances (%) at various wavelengths | | | | |
|---|---|---|---|---|---|---|
| | weight ratio | 500 | 400 | 360 | 320 | 290 |
| Comparative Example 1 | 84/16/0 | 69.89 | 55.67 | 24.99 | 11.20 | 12.02 |
| Comparative Example 2 | 64/36/0 | 57.51 | 42.36 | 14.13 | 7.13 | 7.94 |

TABLE 4-continued

| | Wavelength (nm) $SiO_2/TiO_2/ZnO$ | Transmittances (%) at various wavelengths | | | | |
|---|---|---|---|---|---|---|
| | weight ratio | 500 | 400 | 360 | 320 | 290 |
| Comparative Example 3 | 92/8/0 | 83.57 | 72.55 | 55.97 | 32.65 | 34.23 |
| Comparative Example 4 | 84/0/16 | 93.90 | 88.30 | 39.34 | 40.76 | 41.03 |
| Comparative Example 5 | 64/0/36 | 90.57 | 81.62 | 22.68 | 24.29 | 24.86 |
| Comparative Example 6 | 92/0/8 | 95.83 | 92.09 | 52.87 | 52.80 | 53.65 |

TABLE 5

| | Wavelength (nm) $SiO_2/TiO_2/ZnO$ weight ratio (incorporated in | Transmittances (%) at various wavelengths | | | | |
|---|---|---|---|---|---|---|
| | the particles) | 500 | 400 | 360 | 320 | 290 |
| Comparative Example 7 | 65/35/0 | 50.40 | 36.62 | 8.35 | 5.12 | 6.64 |
| Comparative Example 8 | 55/0/45 | 75.69 | 62.92 | 26.31 | 26.68 | 27.39 |
| Example 2 | 64/36/0 | 55.66 | 40.58 | 9.91 | 4.66 | 5.23 |

EXAMPLE 15

Into an autoclave, 2,688 g of silica hydrogel having an average particle size of 3.0 mm ($SiO_2$: 18.6 wt %) and 199 g of an aqueous sodium hydroxide solution (NaOH: 48.0 wt %) were charged so that the total $SiO_2/Na_2O$ molar ratio in the system would be 7.0, and 1,114 g of deionized water was added thereto, whereupon hydrothermal treatment was carried out at 180° C. for 8 hours with stirring at 20 rpm. The total silica concentration in the system was 12.5 wt %, as $SiO_2$.

The silica hydrogel as starting material was prepared as follows. Namely, water glass of JIS No. 3 diluted with water was instantaneously mixed with sulfuric acid to bring the pH to 8 and to obtain a sol, which was then immediately discharged from the forward end of a nozzle into air, so that it was gelled in air while it was staying in air for about 1 second. At the falling site, an aging tank containing water at room temperature, was placed, so that the formed gel fell therein and was aged. Then, the pH was adjusted to 6 by an addition of sulfuric acid, followed by washing with water to obtain a silica hydrogel which had a particle size of from 2 to 6 mm in diameter and which was sieved for use.

The obtained hydrothermally treated product was subjected to filtration and washing with water, followed by drying by means of a medium fluidized bed dryer to obtain 365 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3°, which correspond to ASTM Card No. 31-1233, peaks corresponding to ASTM Card Nos. 35-63 and 25-1332, were observed. Further, the oil absorption (JIS K5101) of the fine powder was measured and found to be 104 ml/100 g.

The shape of the product was observed by SEM, whereby the shapes of the primary particles were scaly, and it was observed that such scaly primary particles were randomly stacked to form silica agglomerates having voids. The average thickness of the scaly primary particles was 0.05 μm, and the average maximum length of scales was 4.5 μm, and thus the aspect ratio of the average maximum length to the thickness was 90. The average minimum length of the scales was 1.4 μm, and the aspect ratio of the average minimum length to the thickness was accordingly 28.

Further, the amount of free crystalline silicic acid in the fine powder was measured by an X-ray diffraction analysis and found to be less than the detectable limit (less than 2%).

EXAMPLE 16

Into an autoclave, 941 g of silica hydrogel ($SiO_2$: 30.5 wt %) having a particle size of 0.5 mm and 1,023 g of an aqueous sodium silicate solution ($SiO_2$: 20.84 wt %, $Na_2O$: 7.22 wt %, $SiO_2/Na_2O$=2.98 mol/mol) were charged so that the total $SiO_2/Na_2O$ molar ratio in the system would be 7.0, and 2,036 g of deionized water was added thereto, whereupon hydrothermal treatment was carried out at 180° C. for 8 hours with stirring at 20 rpm. The total silica concentration in the system was 12.5 wt % as $SiO_2$.

The silica hydrogel as starting material was one prepared by roughly pulverizing the one used in Example 15 and at the same time drying it to adjust the water content.

The hydrothermally treated product was subjected to filtration and washing with water, followed by drying by means of a medium fluidized bed dryer to obtain 375 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 98 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.06 μm, and the average maximum length of scales was 6.0 μm, and thus the aspect ratio of the average maximum length to the thickness was 100. The average minimum length of the scales was 1.5 μm, and the aspect ratio of the average minimum length to the thickness was accordingly 25.

Further, the amount of free crystalline silicic acid in the fine powder was measured by an X-ray diffraction analysis and found to be less than the detectable limit (less than 2%).

EXAMPLE 17

Into an autoclave, 1,515 g of silica hydrogel ($SiO_2$: 33.0 wt %) having a particle size of 0.5 mm and 199 g of an aqueous sodium hydroxide solution (NaOH: 48.0 wt %) were charged so that the total $SiO_2/Na_2O$ molar ratio in the system would be 7.0, and 2,286 g of deionized water was added thereto. Then, 0.5 g of seed crystals were added thereto, and hydrothermal treatment was carried out at 180° C. for 8 hours while stirring at 20 rpm.

The silica hydrogel as starting material was one obtained by roughly pulverizing the one used in Example 15 and at the same time drying it to adjust the water content.

The seed crystals were preliminarily prepared silica, the shapes of the primary particles of which were scaly, and as a result of the powder X-ray diffraction spectrum, it was found to comprise silica-X characterized by the main peaks at 2θ=4.9 and 26.0° which correspond to ASTM Card No. 16-0380 and a substance which corresponds to ASTM Card Nos. 31-1234 and 37-0386. The total silica concentration in the system was 12.5 wt % as $SiO_2$.

The hydrothermally treated product was subjected to filtration and washing with water, followed by drying by means of a medium fluidized bed dryer to obtain 360 g of a fine powder.

With respect to the formed fine powder, the formed phase was identified by the powder X-ray diffraction spectrum. As the X-ray diffraction spectrum, in addition to the main peaks of silica-X characterized by the main peaks at 2θ=4.9 and 26.0° which correspond to ASTM Card No. 16-0380, peaks corresponding to ASTM Card Nos. 31-1234 and 37-0386 were observed. Further, the oil absorption (JIS K5101) of the fine powder was measured and found to be 98 ml/100 g.

The shape of the product was observed by SEM, whereby the shapes of the primary particles were scaly, and it was observed that such scaly primary particles were randomly stacked to form silica agglomerates having voids. The average thickness of the scaly primary particles was 0.05 μm, and the average maximum length of scales was 5.5 μm, and thus the aspect ratio of the average maximum length to the thickness was 110. The average minimum length of the scales was 1.5 μm, and the aspect ratio of the average minimum length to the thickness was accordingly 30.

Further, the amount of free crystalline silicic acid in the fine powder was measured by an X-ray diffraction analysis and found to be less than the detectable limit (less than 2%).

EXAMPLE 18

Into an autoclave, 592 g of a silica hydrogel ($SiO_2$: 48.5 wt %) having a particle size of 3.0 mm and 1,023 g of an aqueous sodium silicate solution ($SiO_2$: 20.84 wt %, $Na_2O$: 7.22 wt %, $SiO_2/Na_2O$=2.98 mol/mol) were charged so that the total $SiO_2/Na_2O$ molar ratio in the system would be 7.0, and 2,385 g of deionized water was added thereto. Then, 0.5 g of the same seed crystals as used in Example 17 were added thereto, and hydrothermal treatment was carried out at 180° C. for 10 hours while stirring at 20 rpm. The total silica concentration in the system was 12.5 wt % as $SiO_2$.

The silica hydrogel as starting material was one prepared by sieving the one prepared in Example 15 and drying it to adjust the water content.

The hydrothermally treated product was subjected to filtration and washing with water, followed by drying by means of a medium fluidized bed dryer to obtain 380 g of a fine powder.

With respect to the formed fine powder, the formed phase was identified by the powder X-ray diffraction spectrum. As the X-ray diffraction spectrum, in addition to the main peaks of silica-X characterized by the main peaks at 2θ=4.9° and 26.0° which correspond to ASTM Card No. 16-0380, peaks corresponding to ASTM Card Nos. 31-1234 and 37-0386 were observed. Further, the oil absorption (JIS K5101) of the fine powder was measured and found to be 110 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.06 μm, and the average maximum length of scales was 5.5 μm, and thus, the aspect ratio of the average maximum length to the thickness was 92. The average minimum length of the scales was 1.7 μm, and the aspect ratio of the average minimum length to the thickness was accordingly 28.

Further, the amount of free crystalline silicic acid in the fine powder was measured by an X-ray diffraction analysis and found to be less than the detectable limit (less than 2%).

EXAMPLE 19

Into an autoclave, 2,439 g of a silica hydrogel ($SiO_2$: 20.5 wt %) having a particle size of 3.0 mm and 199 g of a sodium hydroxide aqueous solution (NaOH: 48.0 wt %) were charged so that the total $SiO_2/Na_2O$ molar ratio in the system would be 7.0, and 1,362 g of deionized water was added thereto. Then, 0.5 g of seed crystals were added thereto, and hydrothermal treatment was carried out at 180° C. for 8 hours while stirring at 20 rpm. The seed crystals were preliminarily prepared silica, the shapes of the primary particles of which were scaly, and as a result of the powder X-ray diffraction spectrum, it was found to comprise silica-Y characterized by the main peaks at 2θ=5.6°, 25.8° and 28.3° which correspond to ASTM Card No. 31-1233 and a substance corresponding to ASTM Card Nos. 35-63 and 25-1332. The total silica concentration in the system was 12.5 wt % as $SiO_2$.

The silica hydrogel as starting material was one obtained by sieving the one prepared in Example 15 and drying it to adjust the water content.

The hydrothermally treated product was subjected to filtration and washing with water, followed by drying by means of a medium fluidized bed dryer to obtain 368 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 99 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.07 μm, and the average maximum length of scales was 5.4 μm, and thus, the aspect ratio of the average maximum length to the thickness was 77. The average minimum length of the scales was 1.8 μm, and the aspect ratio of the average minimum length to the thickness was 26.

Further, the amount of free crystalline silicic acid in the fine powder was measured by an X-ray diffraction analysis and found to be less than the detectable limit (less than 2%).

EXAMPLE 20

Into an autoclave, 1,543 g of a silica hydrogel ($SiO_2$: 18.6 wt %) having a particle size of 3.0 mm and 1,023 g of an aqueous sodium silicate solution ($SiO_2$: 20.84 wt %, $Na_2O$: 7.22 wt %, $SiO_2/Na_2O$=2.98 mol/mol) were charged so that the total $SiO_2/Na_2O$ molar ratio in the system would be 7.0, and 1,435 g of deionized water was added thereto. Then, 0.5 g of the same seed crystals as used in Example 19 were added thereto, and hydrothermal treatment was carried out at 180° C. for 10 hours while stirring at 20 rpm. The total silica concentration in the system was 12.5 wt % as $SiO_2$.

The silica hydrogel as starting material was one prepared in Example 15.

The hydrothermally treated product was subjected to filtration and washing with water, followed by drying by means of a medium fluidized bed dryer to obtain 378 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 96 ml/100 g.

The shape of the product was observed by SEM, whereby it was found that like Example 15, the shapes of the primary particles were scaly, and it was observed that such scaly primary particles were randomly stacked to form silica agglomerates having voids. The average thickness of the scaly primary particles was 0.05 μm, and the average maximum length of scales was 6.0 μm, and thus the aspect ratio of the average maximum length to the thickness was 120. The average minimum length of the scales was 1.4 μm, and the aspect ratio of the average minimum length to the thickness was accordingly 28.

Further, the amount of free crystalline silicic acid in the fine powder, was measured by an X-ray diffraction analysis and found to be less than the detectable limit (less than 2%).

EXAMPLE 21

Into an autoclave, 2,688 g of a silica hydrogel ($SiO_2$: 18.6 wt %) having a particle size of 2.5 mm and 278 g of an aqueous sodium hydroxide solution (NaOH: 48.0 wt %) were charged so that the total $SiO_2/Na_2O$ molar ratio in the system would be 5.0, and 1,034 g of deionized water was added thereto, whereupon hydrothermal treatment was carried out at 180° C. for 6 hours while stirring at 20 rpm.

The silica hydrogel as starting material was one obtained by sieving the one prepared in Example 15. The total silica concentration in the system was 12.5 wt % as $SiO_2$.

The hydrothermally treated product was subjected to filtration and washing with water, followed by drying by means of a medium fluidized bed dryer to obtain 289 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 93 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.05 μm, and the average maximum length of scales was 4.6 μm, and thus, the aspect ratio of the average maximum length to the thickness was 92. The average minimum length of the scales was 1.4 μm, and the aspect ratio of the average minimum length to the thickness was accordingly 28.

Further, the amount of free crystalline silicic acid in the fine powder, was measured by an X-ray diffraction analysis and found to be less than the detectable limit (less than 2%).

EXAMPLE 22

Into an autoclave, 2,688 g of silica hydrogel ($SiO_2$: 18.6 wt %) having a particle size of 2.5 mm and 154 g of an aqueous sodium hydroxide solution (NaOH: 48.0 wt %) were charged so that the total $SiO_2/Na_2O$ molar ratio in the system would be 9.0, and 1,158 g of deionized water was added thereto, whereupon hydrothermal treatment was carried out at 180° C. for 10 hours while stirring at 20 rpm.

The silica hydrogel as starting material was one obtained by sieving the one prepared in Example 15. The total silica concentration in the system was 12.5 wt % as $SiO_2$.

The hydrothermally treated product was subjected to filtration and washing with water, followed by drying by means of a medium fluidized bed dryer to obtain 387 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 97 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.06 μm, and the average maximum length of scales was 5.8 μm, and thus, the aspect ratio of the average maximum length to the thickness was 97. The average minimum length of the scales was 1.7 μm, and the aspect ratio of the average minimum length to the thickness was accordingly 28.

Further, the amount of free crystalline silicic acid in this fine powder was measured by an X-ray diffraction analysis and found to be less than the detectable limit (less than 2%).

EXAMPLE 23

Into an autoclave, 2,688 g of silica hydrogel ($SiO_2$: 18.6 wt %) having a particle size of 2.5 mm and 126 g of an aqueous sodium hydroxide solution (NaOH: 48.0 wt %) were charged so that the total $SiO_2/Na_2O$ molar ratio in the system would be 11.0, and 1,186 g of deionized water was added thereto, whereupon hydrothermal treatment was carried out at 180° C. for 12 hours while stirring at 20 rpm.

The silica hydrogel as starting material was one obtained by sieving the one prepared in Example 15. The total silica concentration in the system was 12.5 wt % as $SiO_2$.

The hydrothermally treated product was subjected to filtration and washing with water, followed by drying by means of a medium fluidized bed dryer to obtain 408 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, a peak corresponding to ASTM Card No. 35-63 was observed. Further, the oil absorption (JIS K5101) of the fine powder was measured and found to be 97 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.07 μm, and the average maximum length of scales was 6.0 μm, and the aspect ratio of the average maximum length to the thickness was 86. The average minimum length of the scales was 1.8 μm, and the aspect ratio of the average minimum length to the thickness was accordingly 26.

Further, the amount of free crystalline silicic acid in the fine powder was measured by an X-ray diffraction analysis and found to be less than the detectable limit (less than 2%).

EXAMPLE 24

Into an autoclave, 1,492 g of silica hydrogel ($SiO_2$: 33.5 wt %) having a particle size of 1.0 mm and 126 g of an aqueous sodium hydroxide solution (NaOH: 48.0 wt %) were charged so that the total $SiO_2/Na_2O$ molar ratio in the system would be 11.0, and 2,382 g of deionized water was added thereto. Then, 0.5 g of the same seed crystals as used in Example 17 were added, and the hydrothermal treatment was carried out at 180° C. for 11 hours while stirring at 20 rpm.

The silica hydrogel as starting material was one obtained by sieving the one prepared in Example 15 and drying it to adjust the water content. The total silica concentration in the system was 12.5 wt % as $SiO_2$.

The hydrothermally treated product was subjected to filtration and washing with water, followed by drying by means of a medium fluidized bed dryer to obtain 415 g of a fine powder.

With respect to the formed fine powder, the formed phase was identified by the powder X-ray diffraction spectrum. As the X-ray diffraction spectrum, in addition to the main peaks of silica-X characterized by the main peaks at 2θ=4.9° and 26.0° which correspond to ASTM Card No. 16-0380, peaks corresponding to ASTM Card Nos. 31-1234 and 37-0386 were observed. Further, the oil absorption (JIS K5101) of the fine powder was measured and found to be 99 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.07 μm, and the average maximum length of scales was 5.5 μm, and thus, the aspect ratio of the average maximum length to the thickness was 79. The average minimum length of the scales was 1.7 μm, and the aspect ratio of the average minimum length to the thickness was accordingly 24.

Further, the amount of free crystalline silicic acid in the fine powder was measured by an X-ray diffraction analysis and found to be less than the detectable limit (less than 2%).

EXAMPLE 25

Into an autoclave, 2,688 g of silica hydrogel ($SiO_2$: 18.6 wt %) having a particle size of 2.0 mm and 199 g of an aqueous sodium hydroxide solution (NaOH: 48.0 wt %) were charged so that the total $SiO_2/Na_2O$ molar ratio in the system would be 7.0, and 1,114 g of deionized water was added thereto, whereupon hydrothermal treatment was carried out at 180° C. for 6 hours while stirring at 50 rpm.

The silica hydrogel as starting material was one obtained by sieving the one prepared in Example 15. The total silica concentration in the system was 12.5 wt % as $SiO_2$.

The hydrothermally treated product was subjected to filtration and washing with water, followed by drying by means of a medium fluidized bed dryer to obtain 358 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 94 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.04 μm, and the average maximum length of scales was 5.4 μm, and thus, the aspect ratio of the average maximum length to the thickness was 135. The average minimum length of the scales was 1.5 μm, and the aspect ratio of the average minimum length to the thickness was accordingly 38.

Further, the amount of free crystalline silicic acid in the fine powder was measured by an X-ray diffraction analysis and found to be less than the detectable limit (less than 2%).

EXAMPLE 26

Into an autoclave, 2,688 g of silica hydrogel ($SiO_2$: 18.6 wt %) having a particle size of 3.0 mm and 199 g of an aqueous sodium hydroxide solution (NaOH: 48.0 wt %) were charged so that the total $SiO_2/Na_2O$ molar ratio in the system would be 7.0, and 1,114 g of deionized water was added thereto, whereupon hydrothermal treatment was carried out at 170° C. for 11 hours while stirring at 20 rpm.

The silica hydrogel as starting material was one used in Example 15. The total silica concentration in the system was 12.5 wt % as $SiO_2$.

The hydrothermally treated product was subjected to filtration and washing with water, followed by drying by means of a medium fluidized bed dryer to obtain 354 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 100 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.05 μm, and the average maximum length of scales was 5.2 μm, and thus, the aspect ratio of the average maximum length to the thickness was 104. The average minimum length of the scales was 1.5 μm, and the aspect ratio of the average minimum length to the thickness was accordingly 30.

Further, the amount of free crystalline silicic acid in the fine powder was measured by an X-ray diffraction analysis and found to be less than the detectable limit (less than 2%).

EXAMPLE 27

Into an autoclave, 2,688 g of silica hydrogel ($SiO_2$: 18.6 wt %) having a particle size of 3.0 mm and 199 g of an aqueous sodium hydroxide solution (NaOH: 48.0 wt %) were charged so that the total $SiO_2/Na_2O$ molar ratio in the system would be 7.0, and 1,114 g of deionized water was added thereto, whereupon hydrothermal treatment was carried out at 160° C. for 12 hours while stirring at 20 rpm.

The silica hydrogel as starting material was one used in Example 15. The total silica concentration in the system was 12.5 wt % as $SiO_2$.

The hydrothermally treated product was subjected to filtration and washing with water, followed by drying by means of a medium fluidized bed dryer to obtain 362 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 96 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.05 μm, and the average maximum length of scales was 5.0 μm, and thus, the aspect ratio of the average maximum length to the thickness was 100. The average minimum length of the scales was 1.7 μm, and the aspect ratio of the average minimum length to the thickness was accordingly 34.

Further, the amount of free crystalline silicic acid in the fine powder was measured by an X-ray diffraction analysis and found to be less than the detectable limit (less than 2%).

EXAMPLE 28

Into an autoclave, 3,725 g of silica hydrogel ($SiO_2$: 18.6 wt %) having a particle size of 0.1 mm and 275 g of an aqueous sodium hydroxide solution (NaOH: 48.0 wt %) were charged so that the total $SiO_2/Na_2O$ molar ratio in the system would be 7.0, and hydrothermal treatment was carried out at 150° C. for 9 hours while stirring at 20 rpm.

The silica hydrogel as starting material was one obtained by pulverizing and sieving the one used in Example 15. The total silica concentration in the system was 17.3 wt % as $SiO_2$.

The hydrothermally treated product was subjected to filtration and washing with water, followed by drying by means of a medium fluidized bed dryer to obtain 371 g of a fine powder.

With respect to the formed fine powder, the formed phase was identified by the powder X-ray diffraction spectrum. As the X-ray diffraction spectrum, in addition to the main peaks of silica-Y characterized by the main peaks at 2θ=5.6°, 25.8° and 28.3° which correspond to ASTM Card No. 31-1233, peaks corresponding to ASTM Card Nos. 35-63 and 25-1332 were observed. Further, the oil absorption (JIS K5101) of the fine powder was measured and found to be 99 ml/100 g.

The shape of the product was observed by SEM, whereby like Example 15, the shapes of the primary particles were scaly, and it was observed that such scaly primary particles were randomly stacked to form silica agglomerates having voids. The average thickness of the scaly primary particles was 0.05 μm, and the average maximum length of scales was 5.2 μm, and thus, the aspect ratio of the average maximum length to the thickness was 104. The average minimum length of the scales was 1.5 μm, and the aspect ratio of the average minimum length to the thickness was accordingly 30.

Further, the amount of free crystalline silicic acid in the fine powder was measured by an X-ray diffraction analysis and found to be less than the detectable limit (less than 2%).

Comparative Example 9

Into an autoclave, 2,688 g of silica hydrogel ($SiO_2$: 18.6 wt %) having a particle size of 3.0 mm and 199 g of an aqueous sodium hydroxide solution (NaOH: 48.0 wt %) were charged so that the total $SiO_2/Na_2O$ molar ratio in the system would be 7.0, and 1,114 g of deionized water was added thereto, whereupon hydrothermal treatment was carried out at 130° C. for 24 hours while stirring at 20 rpm.

The silica hydrogel as starting material was one used in Example 15. The total silica concentration in the system was 12.5 wt % as $SiO_2$.

The hydrothermally treated product was subjected to filtration and washing with water, followed by drying by means of a medium fluidized bed dryer to obtain 362 g of a fine powder.

With respect to the formed fine powder, the formed phase was identified by the powder X-ray diffraction spectrum, whereby no peak other than a broad pattern of amorphous silica, was observed.

The shape of the product was observed by SEM, whereby the shapes of the particles were non-specific, and no scaly particles were observed. It is considered that the temperature for the hydrothermal treatment was too low.

Comparative Example 10

Into an autoclave, 2,688 g of silica hydrogel ($SiO_2$: 18.6 wt %) having a particle size of 3.0 mm and 199 g of an aqueous sodium hydroxide solution (NaOH: 48.0 wt %) were charged so that the total $SiO_2/Na_2O$ molar ratio in the system would be 7.0, and 1,114 g of deionized water was added thereto, whereupon hydrothermal treatment was carried out at 230° C. for 4 hours while stirring at 20 rpm.

The silica hydrogel as starting material was one used in Example 15. The total silica concentration in the system was 12.5 wt % as $SiO_2$.

The hydrothermally treated product was subjected to filtration and washing with water, followed by drying by means of a medium fluidized bed dryer to obtain 370 g of a fine powder.

With respect to the formed fine powder, the formed phase was identified by the powder X-ray diffraction spectrum, whereby in addition to the peaks of silica-X characterized by the main peaks at 2θ=4.9° and 26.0° which correspond to ASTM Card No. 16-0380, a peak of quartz corresponding to ASTM Card No. 33-1161 was distinctly observed.

The shape of the product was observed by SEM, whereby in addition to those having scaly particle shapes, many particles having a rice grain-shape which appeared to be quartz, were observed. It is considered that the temperature for the hydrothermal treatment was so high that the reaction was not controlled, and it was not possible to avoid formation of quartz.

Comparative Example 11

Into an autoclave, 2,688 g of silica hydrogel ($SiO_2$: 18.6 wt %) having a particle size of 2.5 mm and 87 g of an aqueous sodium hydroxide solution (NaOH: 48.0 wt %) were charged so that the total $SiO_2/Na_2O$ molar ratio in the system would be 16.0, and 1,225 g of deionized water was added thereto, whereupon hydrothermal treatment was carried out at 180° C. for 12 hours while stirring at 20 rpm. The total silica concentration in the system was 12.5 wt % as $SiO_2$.

The hydrothermally treated product was subjected to filtration and washing with water, followed by drying by means of a medium fluidized bed dryer to obtain 438 g of a fine powder.

With respect to the formed fine powder, the formed phase was identified by the powder X-ray diffraction spectrum, whereby in addition to the main peaks of silica-X characterized by the main peaks at 2θ=4.9° and 26.0° which correspond to ASTM Card No. 16-0380, a peak of a broad pattern of amorphous silica was observed.

The shape of the product was observed by SEM, whereby in addition to those having scaly particle shapes, many particles having no specific shapes of amorphous silica were observed. It is considered that the amount of alkali was so small that the solubility of silica was not sufficient, and the crystallization speed was slow.

Comparative Example 12

Into an autoclave, 2,688 g of silica hydrogel ($SiO_2$: 18.6 wt %) having a particle size of 2.5 mm and 463 g of an aqueous sodium hydroxide solution (NaOH: 48.0 wt %) were charged so that the total $SiO_2/Na_2O$ molar ratio in the system would be 3.0, and 849 g of deionized water was added thereto, whereupon hydrothermal treatment was carried out at 170° C. for 10 hours while stirring at 20 rpm. The total silica concentration in the system was 12.5 wt % as $SiO_2$.

The hydrothermally treated product was subjected to filtration and washing with water, followed by drying by means of a medium fluidized bed dryer, whereby the yield of a fine powder was 78 g, and thus, the yield was very poor. It is considered that the amount of alkali was so large that most silica dissolved, and no substantial crystallization was carried out.

For the convenience for comparison, the conditions in Examples and Comparative Examples are summarized in Table 6.

TABLE 6

| | Charged hydrogel | | | SiO$_2$/Na$_2$O | Stirring | Aging conditions | | Seed crystals |
|---|---|---|---|---|---|---|---|---|
| | Particle size (mm) | SiO$_2$ (wt %) | Alkali source | molar ratio (mol/mol) | speed (rpm) | Temp. (° C.) | Time (hr) | Type/amount (g) |
| Example 15 | 3.0 | 18.6 | NaOH | 7.0 | 20 | 180 | 8 | Nil |
| Example 16 | 0.5 | 30.5 | Sodium silicate | 7.0 | 20 | 180 | 8 | Nil |
| Example 17 | 0.5 | 33.0 | NaOH | 7.0 | 20 | 180 | 8 | SiO$_2$—X/0.5 |
| Example 18 | 3.0 | 48.5 | Sodium silicate | 7.0 | 20 | 180 | 10 | SiO$_2$—X/0.5 |
| Example 19 | 3.0 | 20.5 | NaOH | 7.0 | 20 | 180 | 8 | SiO$_2$—Y/0.5 |
| Example 20 | 3.0 | 18.6 | Sodium silicate | 7.0 | 20 | 180 | 10 | SiO$_2$—Y/0.5 |
| Example 21 | 2.5 | 18.6 | NaOH | 5.0 | 20 | 180 | 6 | Nil |
| Example 22 | 2.5 | 18.6 | NaOH | 9.0 | 20 | 180 | 10 | Nil |
| Example 23 | 2.5 | 18.6 | NaOH | 11.0 | 20 | 180 | 12 | Nil |
| Example 24 | 1.0 | 33.5 | NaOH | 11.0 | 20 | 180 | 11 | SiO$_2$—X/0.5 |
| Example 25 | 2.0 | 18.6 | NaOH | 7.0 | 50 | 180 | 6 | Nil |
| Example 26 | 3.0 | 18.6 | NaOH | 7.0 | 20 | 170 | 11 | Nil |
| Example 27 | 3.0 | 18.6 | NaOH | 7.0 | 20 | 160 | 12 | Nil |
| Example 28 | 0.1 | 18.6 | NaOH | 7.0 | 20 | 150 | 9 | Nil |
| Comparative Example 9 | 3.0 | 18.6 | NaOH | 7.0 | 20 | 130 | 24 | Nil |
| Comparative Example 10 | 3.0 | 18.6 | NaOH | 7.0 | 20 | 230 | 4 | Nil |
| Comparative Example 11 | 2.5 | 18.6 | NaOH | 16.0 | 20 | 180 | 12 | Nil |
| Comparative Example 12 | 2.5 | 18.6 | NaOH | 3.0 | 20 | 170 | 10 | Nil |

Note: The total silica concentration (SiO$_2$ wt %) was 17.3% in Example 28 only and 12.5% in other Examples.

EXAMPLE 29

The silica agglomerates obtained in Example 15 and titanium dioxide particulates (TTO-55A, tradename, manufactured by Ishihara Sangyo K.K., average particle size: 0.03 to 0.05 µm) were sampled so that the total weight of the two would be 5.0 g, and the weight ratio of silica:titanium dioxide=84 wt %:16 wt %, put into a shaking type powder mixer manufactured by Kabushiki Kaisha Shinmaru Enterprises (Turbler Shaker Mixer T2C Model, tradename, capacity: 100 cm$^3$, containing alumina balls) and mixed for 30 minutes.

The fine powder after mixing (the silica composite of the present invention) was observed by SEM, whereby it was observed that titanium dioxide particulates were supported as very uniformly dispersed on the surfaces, and on the inner surfaces in the voids, of the silica agglomerates. Further, the silica agglomerates were not disintegrated or pulverized as visually confirmed and maintained the initial shapes substantially.

Then, 1.12 g of vaseline and 0.48 g of liquid paraffin were added to 0.4 g of the fine powder and thoroughly dispersed by means of a three-roll mill to obtain a paste. The paste was sandwiched between a pair of quartz plates having a thickness of 2 mm and spreaded until the layer thickness became 25 µm, whereupon the spectral transmittance was measured by an automatic spectrophotometer. A wavelength beyond 400 nm represents the visible light region, and a wavelength within a range of 280 to 400 nm represents the ultraviolet region. The smaller the transmittance in the ultraviolet region, the better the ultraviolet ray-shielding effect. The larger the transmittance in the visible light region, the higher the transparency as observed with naked eyes. At 500 nm, the transmittance was 62.98%, at 400 nm, the transmittance was 47.86%, at 360 nm, the transmittance was 15.88%, at 320 nm, the transmittance was 7.50%, and at 290 nm, the transmittance was 7.97%.

The composite exhibited a characteristic such that the transmittance in the visible light region was fairly high, and yet, the transmittance in the ultraviolet region was low.

EXAMPLE 30

Tests similar to Example 29 were carried out by changing the titanium dioxide particulates to zinc oxide particulates. As the zinc oxide, zinc oxide particulates manufactured by Sumitomo Osaka Cement K.K. (ZnO-310, tradename, average particle size: 0.03 µm) were used, and a composite was formed under the same conditions as in Example 29 except that the blend ratio of silica to the zinc oxide particulates was adjusted to a weight ratio of the silica agglomerates:the zinc oxide particulates=84 wt %:16 wt %, and tested under similar conditions. At 500 nm, the transmittance was 91.75%, at 400 nm, the transmittance was 82.58%, at 360 nm, the transmittance was 24.13%, at 320 nm, the transmittance was 22.90%, and at 290 nm, the transmittance was 21.91%.

The composite exhibited a characteristic such that the transmittance in the visible light region was fairly high, and yet, the transmittance in the ultraviolet region was low.

EXAMPLE 31

A test was carried out in which both of titanium dioxide particulates and zinc oxide particulates were blended to silica agglomerates.

The silica agglomerates obtained in Example 15, titanium dioxide particulates (TTO-51A, tradename, manufactured by Ishihara Sangyo K.K., average particle size: 0.01 to 0.03 µm) and zinc oxide particulates (ZnO-310, tradename, manufactured by Sumitomo Osaka Cement K.K., average particle size: 0.03 µm) were mixed so that the total weight would be 5.0 g, and the weight ratio of the silica agglomerates:the titanium dioxide particulates:the zinc oxide particulates=72 wt %:7 wt %:21 wt %, and a composite was formed under the same conditions as in Example 29 and tested under similar conditions.

At 500 nm, the transmittance was 82.44%, at 400 nm, the transmittance was 70.38%, at 360 nm, the transmittance was 13.25%, at 320 nm, the transmittance was 10.27%, and at 290 nm, the transmittance was 8.86%.

The composite exhibited a characteristic such that it simultaneously has a characteristic that the transmittance in a visible light region is fairly high and yet, the transmittance in the ultraviolet region is low and a characteristic such that the change in transmittance from the ultraviolet region to the visible light region is sharp or abrupt.

EXAMPLE 32

A composite was formed under the same conditions as in Example 29 except that the weight ratio of the silica agglomerates:the titanium dioxide particulates:the zinc oxide particulates=64 wt %:9 wt %:27 wt %, and tested under similar conditions.

At 500 nm, the transmittance was 78.41%, at 400 nm, the transmittance was 65.13%, at 360 nm, the transmittance was 9.37%, at 320 nm, the transmittance was 7.35%, and at 290 nm, the transmittance was 6.72%.

The composite exhibited a characteristic such that it simultaneously has a characteristic that the transmittance in the visible light region is fairly high and yet the transmittance in the ultraviolet region is low and a characteristic that the change in the transmittance from the ultraviolet region to the visible light region is sharp or abrupt.

EXAMPLE 33

A composite was formed under the same conditions as in Example 29 except that the weight ratio of the silica agglomerates:the titanium dioxide particulates:the zinc oxide particulates=56 wt %:8 wt %:36 wt %, and tested under similar conditions.

At 500 nm, the transmittance was 79.05%, at 400 nm, the transmittance was 65.73%, at 360 nm, the transmittance was 9.56%, at 320 nm, the transmittance was 7.70%, and at 290 nm, the transmittance was 6.92%.

The composite exhibited a characteristic such that it simultaneously has a characteristic that the transmittance in the visible light region is fairly high and yet, the transmittance in the ultraviolet region is low and a characteristic that the change in transmittance from the ultraviolet region to the visible light region is sharp or abrupt.

The results of the foregoing Examples 29 to 33 are summarized in Table 7.

TABLE 7

| | Wavelength (nm) $SiO_2/TiO_2/ZnO$ | Transmittances (%) at various wavelengths | | | | |
|---|---|---|---|---|---|---|
| | Weight ratio | 500 | 400 | 360 | 320 | 290 |
| Example 29 | 84/16/0 | 62.98 | 47.86 | 15.88 | 7.50 | 7.97 |
| Example 30 | 84/0/16 | 91.75 | 82.58 | 24.13 | 22.90 | 21.91 |
| Example 31 | 72/7/21 | 82.44 | 70.38 | 13.25 | 10.27 | 8.86 |
| Example 32 | 64/9/27 | 78.41 | 65.13 | 9.37 | 7.35 | 6.72 |
| Example 33 | 56/8/36 | 79.05 | 65.73 | 9.56 | 7.70 | 6.92 |

The silica agglomerates being a matrix for supporting the metal oxide particulates of the present invention are composed of scaly silica, and by virtue of the particle shape, they are basically excellent in the alignment property, the shielding property and the comfortableness in use such as spreadability or extendability.

The metal oxide particulates are essentially extremely fine and accordingly have a strong agglomerating nature. Accordingly, it has been extremely difficult to uniformly disperse them as primary particles in a medium such as a cosmetic, a coating material or a resin by themselves, and it has been difficult to sufficiently obtain their inherent ultraviolet ray-shielding function, etc. Whereas, according to the present invention such metal oxide particulates are supported on the surfaces, and on the inner surfaces in voids, of the silica agglomerates composed of scaly silica, whereby as a whole, they take the most preferred form along the surfaces of the silica particles under a stabilized condition. Accordingly, the silica-metal oxide particulate composite of the present invention is excellent in the ultraviolet ray-shielding effect, etc.

Further, with the composite of the present invention, the decomposing-deteriorating action against an organic compound by a photocatalytic oxidation action which is naturally worried out, is very little in spite of the fact that no positive treatment such as incorporating and complexing the metal oxide particulates into silica particles, as proposed in the prior art, is carried out.

Further, according to the present invention, it is possible to provide a method for producing the silica agglomerates of a specific shape having voids formed by random stacking of scaly silica primary particles, which are useful as a carrier for such metal oxide particulates, by hydrothermal treatment using silica hydrogel as starting material, at a low temperature and in a sufficiently short period of time for industrial operation without conversion to e.g. quartz which brings about a problem in safety against organism.

This method is advantageous in that as compared with silica gel as silica material for conventional hydrothermal treatment, silica hydrogel is so easily chemically disintegratable that it is not necessary to mechanically pulverize it for the hydrothermal treatment and that it can be hydrothermally treated without drying i.e. in the state of hydrogel containing a large amount of water, which is very advantageous from the viewpoint of energy.

In the case of a method wherein silica gel as conventional material is used as starting material, it is disadvantageous that the silica hydrogel has to be once dried by exerting heat energy, and besides, by such drying, bonding of the gel is strengthened so that chemical disintegration will no longer take place (namely, by exerting an extra energy, the hydrogel is inactivated), whereby it will be necessary to again exert mechanical energy for pulverization. Thus, the conventional method has double problems from the viewpoint of energy.

As described in the foregoing, the method of the present invention for producing silica agglomerates useful as a carrier for the metal oxide particulates by hydrothermal treatment of silica hydrogel, is a method which is very useful for industrial application.

What is claimed is:

1. A composite comprising metal oxide particulates and silica agglomerates having voids formed by random stacking of scaly silica primary particles, and metal oxide particulates supported on the surfaces, and the inner surfaces in the voids, of the silica agglomerates.

2. The composite according to claim 1, wherein the scaly silica primary particles have a thickness of about 0.001 to 1 $\mu$m and an aspect ratio of the maximum length of the scale to the thickness of at least 10.

3. The composite according to claim 1, wherein the metal oxide particulates have a primary particle size of from 0.002 to 0.5 $\mu$m.

4. The composite according to claim 1, wherein the amount of the metal oxide particulates in the composite is from 1 to 80 wt %.

5. The composite according to claim 1, wherein the metal oxide particulates have an ultraviolet ray-shielding function.

6. The composite according to claim 5, wherein the metal oxide particulates having an ultraviolet ray-shielding function are particulates of one or more members selected from the group consisting of titanium dioxide, zinc oxide, cerium oxide, iron oxide and zirconium oxide.

7. A carrier consisting essentially of silica agglomerates having voids formed by random stacking of scaly silica primary particles, wherein the surfaces, and the inner surfaces in the voids, of the silica agglomerates, constitute sites for supporting a substance to be supported.

8. A method for producing silica agglomerates as defined in claim 7, which comprises subjecting silica hydrogel to hydrothermal treatment in the presence of an alkali metal salt to form silica agglomerates wherein scaly silica primary particles are randomly stacked, wherein the temperature for the hydrothermal treatment is from 150 to 220° C., and the molar ratio of total silica/alkali $SiO_2/Me_2O$, wherein Me is an alkali metal, in the treatment liquid is from 4 to 15 mol/mol.

9. The method according to claim 8, wherein the $SiO_2$ concentration in the silica hydrogel is from 15 to 75 wt %.

10. The method according to claim 8, wherein the total silica concentration in the treatment liquid subjected to the hydrothermal treatment, is from 1 to 30 wt % as $SiO_2$.

11. The method according to claim 8, wherein the hydrothermal treatment is carried out for from 5 to 50 hours.

12. The method according to claim 8, wherein the hydrothermal treatment is carried out in the presence of seed crystals.

13. The method according to claim 8, wherein the amount of free crystalline silicic acid as measured by an X-ray diffraction analysis of the silica agglomerates, is less than 10%.

14. The composite according to claim 2, wherein the thickness of the primary scaly silica particles is from 0.01 to 0.5 µm and an aspect ratio of at least 30.

15. A method for producing the silica-metal oxide particular composite as defined in claim 1, which comprises subjecting silica hydrogel to hydrothermal treatment in the presence of an alkali metal salt to form silica agglomerates wherein scaly silica primary particles are randomly stacked, wherein the temperature for the hydrothermal treatment is from 150 to 220° C., and the molar ratio of total $SiO_2/Me_2O$, wherein Me is an alkali metal, in the treatment liquid is from 4 to 15 mol/mol, and then adding and mixing metal oxide particulates to the silica agglomerates.

16. The method according to claim 15, wherein the $SiO_2$ concentration in the silica hydrogel is from 15 to 75 wt %.

17. The method according to claim 15, wherein the total silica concentration in the treatment liquid subjected to the hydrothermal treatment, is from 1 to 30 wt % as $SiO_2$.

18. The method according to claim 15, wherein the hydrothermal treatment is carried out for from 5 to 50 hours.

19. The method according to claim 15, wherein the hydrothermal treatment is carried out in the presence of seed crystals.

20. The method according to claim 15, wherein the amount of free crystalline silicic acid as measured by an X-ray diffraction analysis of the silica agglomerates, is less than 10%.

* * * * *